United States Patent
Menasche et al.

(10) Patent No.: US 8,361,796 B2
(45) Date of Patent: Jan. 29, 2013

(54) METHOD FOR GENERATING PRIMATE CARDIOVASCULAR PROGENITOR CELLS FOR CLINICAL USE FROM PRIMATE EMBRYONIC STEM CELLS OR EMBRYONIC-LIKE STATE CELLS, AND THEIR APPLICATIONS

(75) Inventors: Philippe Menasche, Paris (FR); Michel Puceat, Champcueil (FR); Jérôme Larghero, Boulogne-Billancourt (FR); Guillaume Blin, Paris (FR); David Nury, Corbeil (FR); Sonia Stefanovic, Draveil (FR)

(73) Assignees: Assistance Publique—Hopitaux de Paris, Paris (FR); Institut National de la Sante et de la Recherche Medicale (Inserm), Paris (FR); Universite Paris Descartes, Paris (FR); Universite Paris Diderot Paris 7, Paris (FR)

( * ) Notice: Subject to any disclaimer, the term of this patent is extended or adjusted under 35 U.S.C. 154(b) by 32 days.

(21) Appl. No.: 12/921,908

(22) PCT Filed: Mar. 10, 2009

(86) PCT No.: PCT/EP2009/052797
§ 371 (c)(1),
(2), (4) Date: Sep. 10, 2010

(87) PCT Pub. No.: WO2009/112496
PCT Pub. Date: Sep. 17, 2009

(65) Prior Publication Data
US 2011/0014691 A1    Jan. 20, 2011

Related U.S. Application Data

(60) Provisional application No. 61/035,146, filed on Mar. 10, 2008.

(30) Foreign Application Priority Data

Mar. 10, 2008    (EP) .................................... 08300138

(51) Int. Cl.
*C12N 5/00*    (2006.01)
*C12N 5/02*    (2006.01)
(52) U.S. Cl. ........................................ 435/377; 435/325
(58) Field of Classification Search .................. 435/377, 435/325
See application file for complete search history.

(56) References Cited

U.S. PATENT DOCUMENTS
2003/0022367 A1    1/2003    Xu

FOREIGN PATENT DOCUMENTS
WO    WO 2007/070964 A1    6/2007

OTHER PUBLICATIONS

Amit et al., "Derivation and maintenance of human embryonic stem cells", Methods Mol Biol., 2006, pp. 43-53, vol. 331, Humana Press Inc., NJ.
Andrée et al., "BMP-2 induces ectopic expression of cardiac lineage markers and interferes with somite formation in chicken embryos", Mech Dev., 1998, pp. 119-131, vol. 70, Elsevier Science Ireland, Ltd.
Balsam et al., "Haematopoietic stem cells adopt mature haematopoietic fates in ischaemic myocardium", Nature, 2004, pp. 668-673, vol. 426.
Behfar et al., "Stem cell differentiation requires a paracrine pathway in the heart", FASEB J., 2002, pp. 1558-1566, vol. 16.
Behfar et al., "Cardiopoietic programming of embryonic stem cells for tumor-free heart repair", J Exp Med., 2007, pp. 405-420, vol. 204, No. 2, The Rockefeller University Press.
Beltrami et al., "Evidence that human cardiac myocytes divide after myocardial infarction", N Engl J Med., 2001, pp. 1750-1757, vol. 344, No. 23.
Breckenridge et al., "A role for BMP signalling in heart looping morphogenesis in Xenopus", Dev Biol., 2001, pp. 191-203, vol. 232, Academic Press.
Bushway et al., "High-throughput screening for modulators of stem cell differentiation", Methods Enzymol., 2006, pp. 300-316, vol. 414, Elsevier Inc.
Cezar, "Can human embryonic stem cells contribute to the discovery of safer and more effective drugs?", Curr Opin chem Biol., 2007, pp. 405-409, vol. 11.
Cowan et al., "Derivation of embryonic stem-cell lines from human blastocysts", N Engl J Med., 2004, pp. 1353-1356, vol. 350, Mass. Med. Society.
Damjanov et al., "Teratocarcinogenesis as related to the age of embryos grafted under the kidney capsule", Wilhelm Roux Archiv., 1971, pp. 288-290, vol. 167, Springer-Verlag.
Frasch, "Intersecting signalling and transcriptional pathways in *Drosophila* heart specification", Semin Cell Dev Biol., 1999, pp. 61-71, vol. 10, Academic Press.
Greber et al., "Fibroblast growth factor 2 modulates transforming growth factor β signaling in mouse embryonic fibroblasts and human ESCs (hESCs) to support hESC self-renewal", Stem Cells, 2006, pp. 455-464, vol. 25.
Janssens et al., "Autologous bone marrow-derived stem-cell transfer in patients with ST-segment elevation myocardial infarction double-blind, randomised controlled trial", Lancet, 2006, pp. 113-121, vol. 367.
Kehat et al., "Electromechanical integration of cardiomyocytes derived from human embryonic stem cells", Nat Biotechnol., 2004, pp. 1282-1289, vol. 22, No. 10.

(Continued)

*Primary Examiner* — Marcia S Noble
(74) *Attorney, Agent, or Firm* — Buchanan Ingersoll & Rooney P.C.

(57) ABSTRACT

The present invention is directed to a method for the in vitro preparation of cardiovascular progenitors cells from mammalian embryonic stem cells (ES cells) or mammalian embryonic-like state cells, preferably from primate, wherein said method comprises the use of the CD15 (SSEAI) marker as a positive cardiovascular progenitors differentiation marker. The present invention also claimed the use of a receptor tyrosine kinase inhibitor, particularly the SU5402 or SU11248 in association with the BMP2 for improving the efficiency of the desired differentiation. The present invention is also directed to the use of platelet lysate as foetal animal serum substitute in a culture medium intended to the proliferation or propagation of primate ES cells maintaining their pluripotency feature. Derived compositions or kits in relation with the claimed methods or product obtainable by the claimed methods form also part of the present invention.

17 Claims, 18 Drawing Sheets

OTHER PUBLICATIONS

Figure 1:
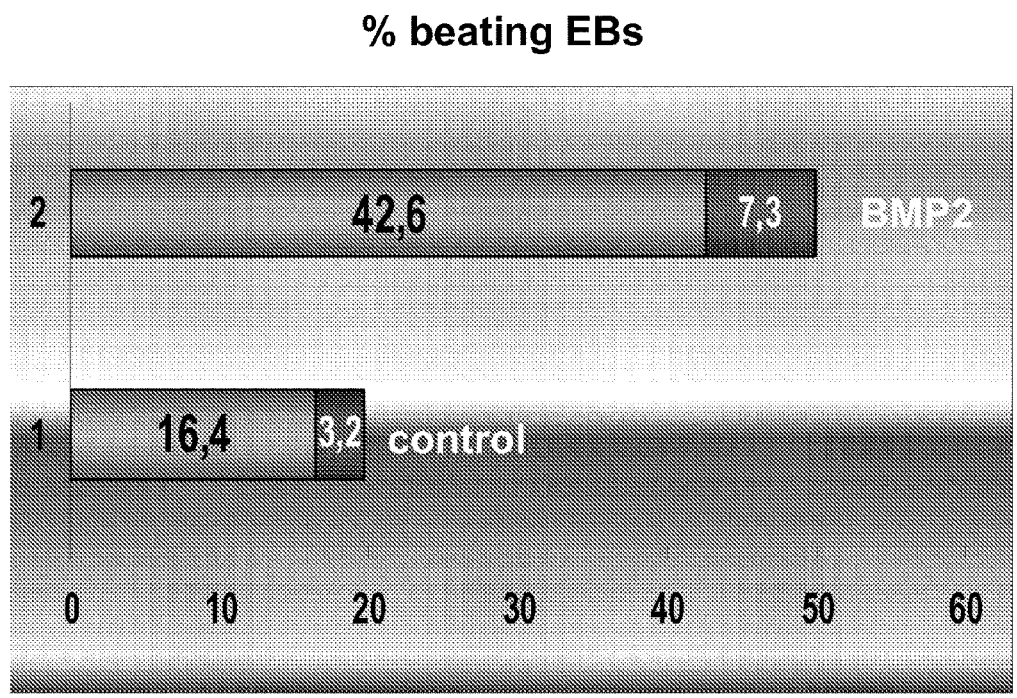

Kofidis et al., "Allopurinol/uricase and ibuprofen enhance engraftment of cardiomyocyte-enriched human embryonic stem cells and improve cardiac function following myocardial injury", Eur J Cardiothorac Surg., 2006, pp. 50-55, vol. 29, Elsevier B.V.

Kolossov et al., "Engraftment of engineered ES cell-dervived cardiomyocytes but not BM cells restores contractile function to the infarcted myocardium", J Exp Med., 2006, pp. 2315-2327, vol. 203, No. 10, The Rockefeller University Press.

Laflamme et al.,"Formulation of human myocardium in the rat heart from human embryonic stem cells", Am J Pathol., 2005, pp. 663-671, vol. 167, No. 3, Am. Society for Investigative Pathology.

Laflamme et al., "Regenerating the heart", Nat Biotechnol., 2005, pp. 845-856, vol. 23, No. 7.

Lagostena et al., "Electrophysiological properties of mouse bone marrow c-kit+ cells co-cultured onto neonatal cardiac myocytes", Cardiovasc Res., 2005, pp. 482-492, vol. 66, Elsevier B.V.

Léobon et al., "Myoblasts transplanted into rat infarcted myocardium are funtionally isolated from their host", Proc Nat'l Acad Sci, USA., 2003, pp. 7808-7811, vol. 100, No. 13.

Lunde et al., "Intracoronary injection of mononuclear bone marrow cells in acute myocardial infarction", N Engl J Med., 2006, pp. 1199-1209, vol. 355, No. 12, Mass. Med. Society.

Maherali et al., "A high-efficiency system for the generation and study of human induced pluripotent stem cells", Cell Stem Cell, 2008, pp. 340-345, vol. 3, Elsevier Inc.

Massagué et al., "Integration of Smad and MAPK pathways: a link and a linker revisited", Genes Dev., 2003, pp. 2993-2997, vol. 17, Cold Spring Harbor Lab. Press.

Ménard et al., "Transplantation of cardiac-committed mouse embryonic stem cells to infarcted sheep myocardium: a preclinical study", Lancet, 2005, pp. 1005-1012, vol. 366.

Ménard et al., "Transfer of mouse embryonic stem cells to sheep myocardium", Lancet, 2006, pp. 301-302, vol. 367.

Meyer et al., "Intracoronary bone marrow cell transfer after myocardial infarction", Circulation, 2006, pp. 1287-1294, vol. 113.

Mitalipov et al., "Isolation and characterization of novel rhesus monkey embryonic stem cell lines", Stem Cells, 2006, pp. 2177-2186, vol. 24.

Murry et al., Haematopoietic stem cells do not transdifferentiate into cardiac myocytes in myocardial infarcts, Nature, 2004, pp. 664-668, vol. 428.

Nakagawa et al., "Generation of induced pluripotent stem cells without myc from mouse and human fibroblasts", Nat Biotechnol., 2008, pp. 101-106, vol. 26, No. 1.

Pal et al., "Similar pattern in cardiac differentiation of human embryonic stem cell lines, BGO1V and ReliCell® hES1, under low serum concentration supplemented with bone morphogenetic protein-2", Differentiation, 2007, pp. 112-122, vol. 75.

Pera et al., "Human embryonic stem cells: prospects for development", Development, 2004, pp. 5515-5525, vol. 131.

Pfaffl, "A new mathematical model for relative quantification in real-time RT-PCR", Nucleic Acids Res., 2001, pp. 2002-2007, vol. 29, No. 9.

Puceat et al., "Embryonic stem cells: from bench to bedside", Clin Pharmacol Ther., 2007, pp. 337-339, vol. 82, No. 3.

Reinecke et al., "Skeletal muscle stem cells do not transdifferentiate into cardiomyocytes after cardiac grafting", J Mol Cell Cardiol., 2002, pp. 241-249, vol. 34.

Reiter et al., "Bmp2b and Oep promote early myocardial differentiation through their regulation of *gata5*", Dev Biol., 2001, pp. 330-338, vol. 234, Academic Press.

Resenzweig, "Cardiac cell therapy—mixed results from mixed cells", N Engl J Med., 2006, pp. 1274-1277, vol. 355.

Schächinger et al., "Intracoronary bone marrow-derived progenitor cells in acute myocardial infarction", N Engl J Med., 2006, pp. 1210-1221, vol. 355.

Shi et al., "BMP signalling is required for heart formation in vertebrates", Dev Biol., 2000, pp. 226-237, vol. 224, Academic Press.

Singla et al., "Transplantation of embryonic stem cells into the infarcted mouse heart: formation of multiple cell types", J Mol Cell Cardiol., 2006, pp. 195-200, vol. 40, Elsevier Ltd.

Smith, "Embryo-derived stem cells: of mice and men", Annu Rev Cell Dev Biol., 2001, pp. 435-462, vol. 17, Annual Reviews.

Stefanovic et al., "Not just a gatekeeper of pluripotency for embryonic stem cell, a cell fate instructor through a gene dosage effect", Cell Cycle, 2007, pp. 8-10, vol. 6, Issue 1.

Teichmann et al., "Highly restricted *BMP10* expression in the trabeculating myocardium of the chick embryo", Dev Genes Evol, 2004, pp. 96-98, vol. 214.

Teng et al., "Massive mechanical loss of microspheres with direct intramyocardial injection in the beating heart: implications for cellular cardiomyoplasty", J Thorac Cardiovasc Surg., 2006, pp. 628-632, vol. 132.

Wernig et al., "In vitro reprogramming of fibroblasts into a pluripotent ES-cell like-state", Nature, 2007, pp. 318-324, vol. 448, No. 7151.

Yao et al., "Long-term self-renewal and directed differentiation of human embryonic stem cells in chemically defined conditions", Proc Nat'l Acad Sci, USA., 2006, pp. 6907-6912, vol. 103, No. 18.

Zeineddine et al., "Oct-3/4 dose dependently regulates specification of embryonic stem cells toward a cardiac lineage and early heart development", Dev Cell., 2006, pp. 535-546, vol. 11, Elsevier Inc.

Leschik et al., "Cardiac commitment of primate embryonic stem cells", Nature Protocols, 2008, pp. 1381-1387, vol. 3, No. 9.

Puceat et al., "Protocols for cardiac differentiation of embryonic stem cells", Methods, 2008, pp. 168-171, vol. 45, Elsevier Inc.

Li et al., "Transplantation of human embryonic stem cell-derived endothelial cells for vascular diseases", J Cell Biochem., 2009, pp. 194-199, vol. 106.

Tomescot et al., "Differentiation in vivo of cardiac committed human embryonic stem cells in postmyocardial infarcted rats", Stem Cells, 2007, pp. 2200-2205, vol. 25.

Draper et al., "Surface antigens of human embryonic stem cells: changes upon differentiation in culture", J Anat., 2002, pp. 249-258, vol. 200.

Henderson et al., "Preimplantation human embryos and embryonic stem cells show comparable expression of stage-specific embryonic antigens", Stem Cells, 2002, pp. 329-337, vol. 20.

Thomson et al., "Embryonic stem cells lines derived from human blastocysts", Science, 1998, pp. 1145-1147, vol. 282.

Stewart et al., "Mechanisms of self-renewal in human embryonic stem cells", European J of Cancer, 2006, pp. 1257-1272, vol. 42.

Levenberg et al., "Endothelial cells derived from human embryonic stem cells", PNAS, 2002, pp. 4391-4396, vol. 99, No. 7.

Ferreira et al., "Vascular progenitor cells isolated from human embryonic stem cells give rise to endothelial and smooth muscle-like cells and form vascular networks in vivo", Circulation Research, 2007, pp. 286-294, vol. 101.

Yamahara et al., "Augmentation of neovascularizaiton in Hindlimb ischemia by combined transplantation of human embryonic stem cells-derived endothelial and mural cells", PLos ONE, 2008, pp. 1-11, vol. 3, Issue 2.

Bai et al., "Directing human embryonic stem cells to generate vascular progenitor cells", Gene Therapy, 2008, pp. 89-95, vol. 15.

Singla et al., "Enhancement by growth factors of cardiac myocyte differentiation from embryonic stem cells: A promising foundation for cardiac regeneration", Biochem and Biophys Res Comm., 2005, pp. 637-642, vol. 335, Elsevier, Inc.

Kawai et al., "Efficient cardiomyogenic differentiation of embryonic stem cells by fibroblast growth factor 2 and bone morphogenetic protein 2", Circ J., 2004, pp. 691-702, vol. 68.

Wei, 2005, "Embryonic stem cells and cardiomyocyte differentiation: phenotype and molecular analyses", J Cell Mol Med., pp. 804-817, vol. 9, No. 4.

Schultheiss et al., "A role for bone morphogenetic proteins in the induction of cardiac myogenesis", Genes & Development, 1997, pp. 451-462, vol. 11.

Améen et al., "Human embryonic stem cells: current technologies and emerging industrial applications", Oncology Hematology, 2008, pp. 54-80, vol. 65, Elsevier, Ireland Ltd.

Emre et al., "A chemical approach to stem cell biology", Curr Opin in Chem Biol., 2007, pp. 252-258, vol. 11, Elsevier, Inc.

Tseng et al., "The GSK-3 inhibitor BIO promotes proliferation in Mammalian Cardiomyocytes", Chem & Biol., 2006, pp. 957-963, vol. 13, Elsevier, Inc.

Schallmoser et al., "Human platelet lysate can replace fetal bovine serum for clinical-scale expansion of functional mesenchymal stromal cells", Transfusion, 2007, pp. 1436-1446, vol. 47.

Yan et al., "Cyclosporin—A potently induces highly cardiogenic progenitors from embryonic stem cells", Biochemical and Biophysical Research Comm., 2009, pp. 115-120, vol. 379, Elsevier, Inc.

Perino et al., "Cardiomyogenic stem an progenitor cell plasticity and the dissection of cardiopoiesis", J of Molecular Cellular Cardiology, 2008, pp. 475-494, vol. 45, Elsevier, Inc.

Habib et al., "Human embryonic stem cells for cardiomyogenesis", J of Molecular Cellular Cardiology, 2008, pp. 462-474, vol. 45, Elsevier, Inc.

Takahashi et al., "Induction of pluripotent stem cells from mouse embryonic and adult fibroblast cultures by defined factors", Cell, 2006, pp. 663-676, vol. 126, Elsevier, Inc.

Takahashi et al., "Induction of pluripotent stem cells from adult human fibroblasts by defined factors," Cell, 2007, pp. 861-872, vol. 131, Elsevier, Inc.

Amit et al., "No evidence for infection of human embryonic stem cells by feeder cell-derived murine leukemia viruses", Stem Cells, 2005, pp. 761-771, vol. 23.

Figure 11A:
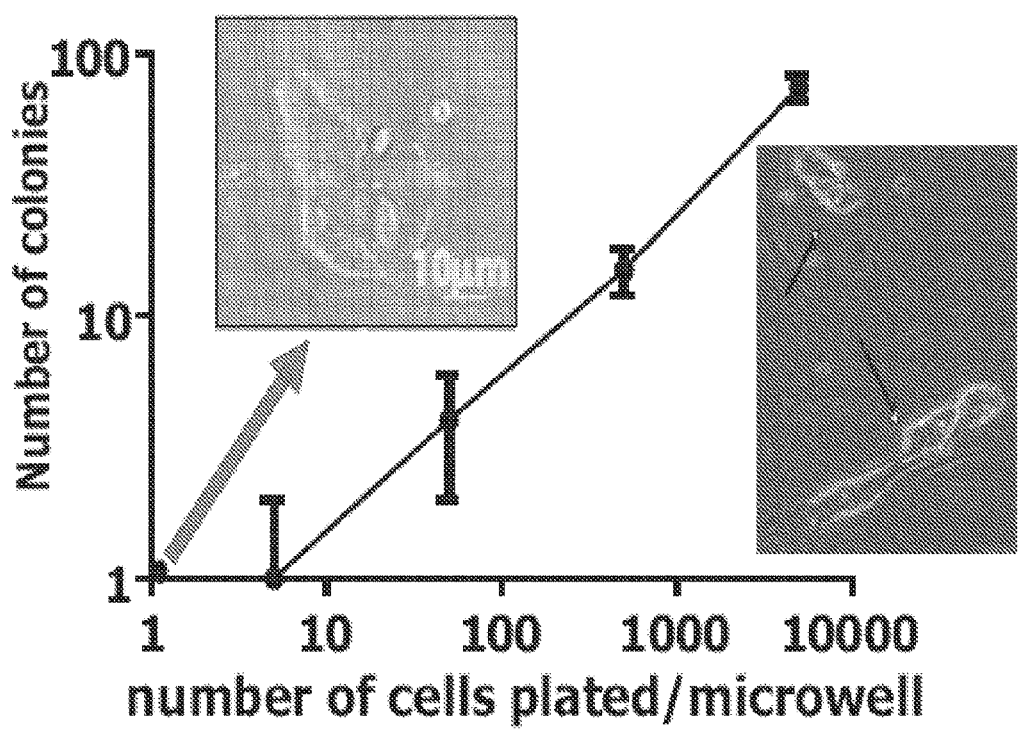
Figure 11B:
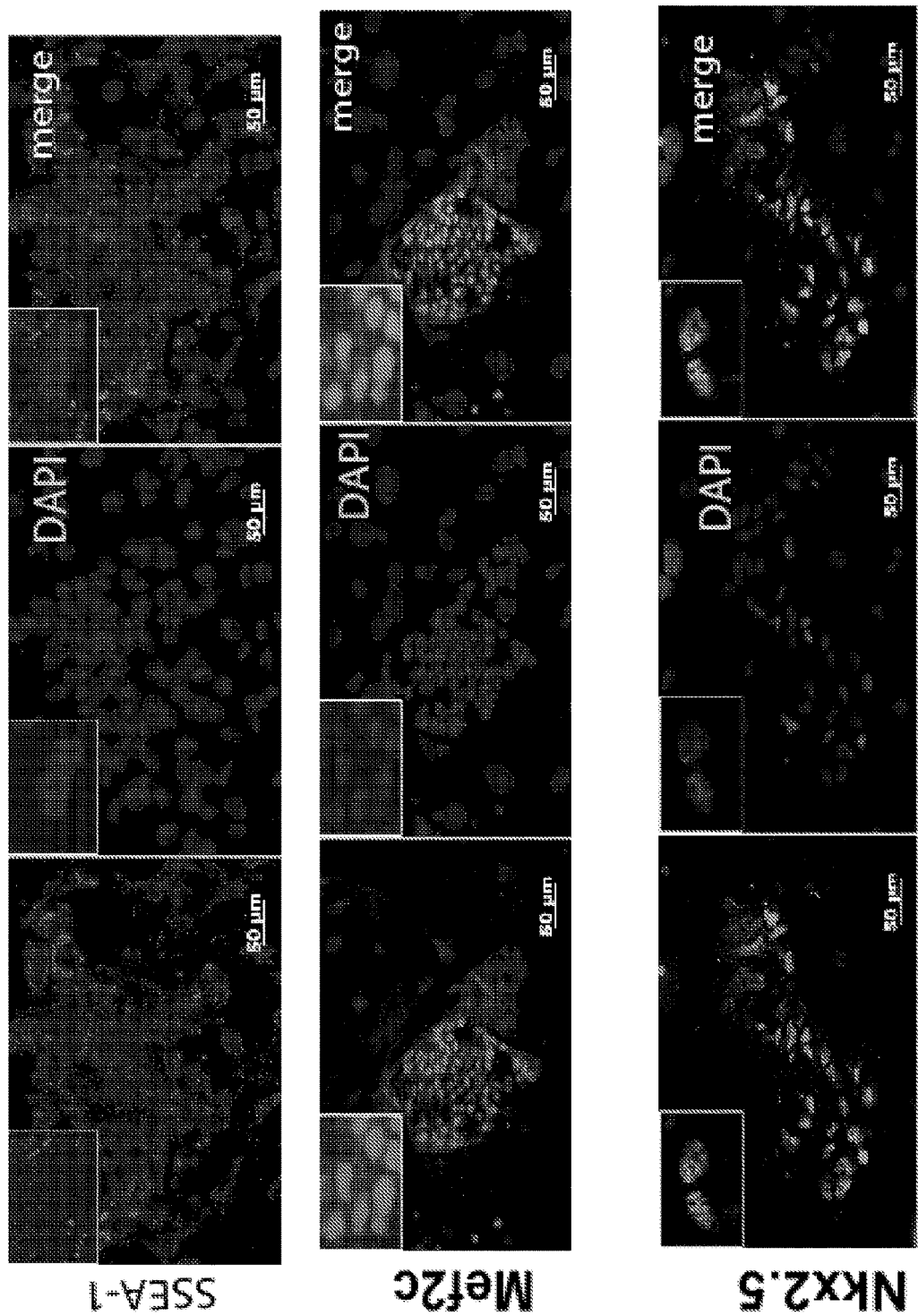

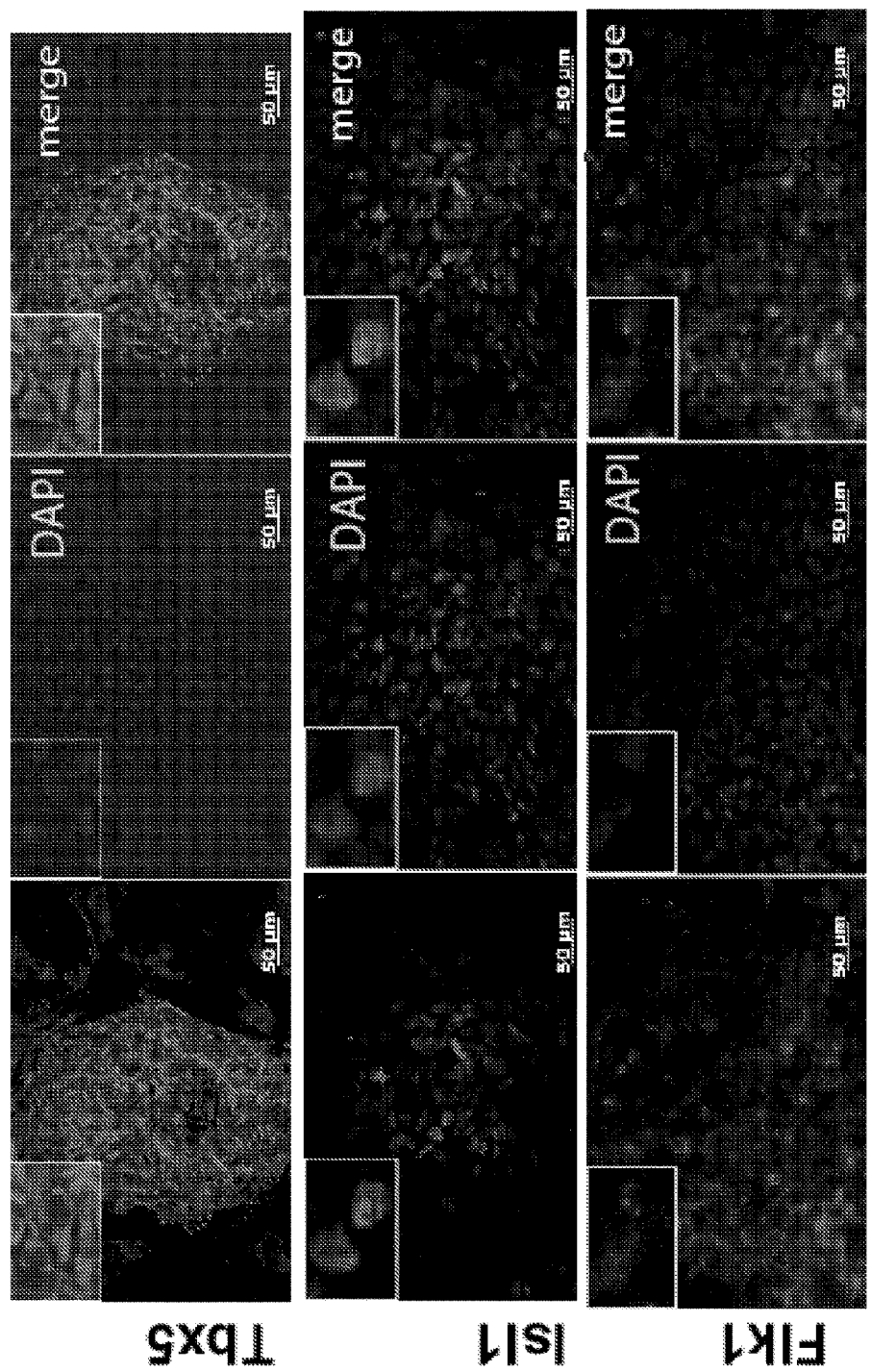
FIGURE 11B(continuing)

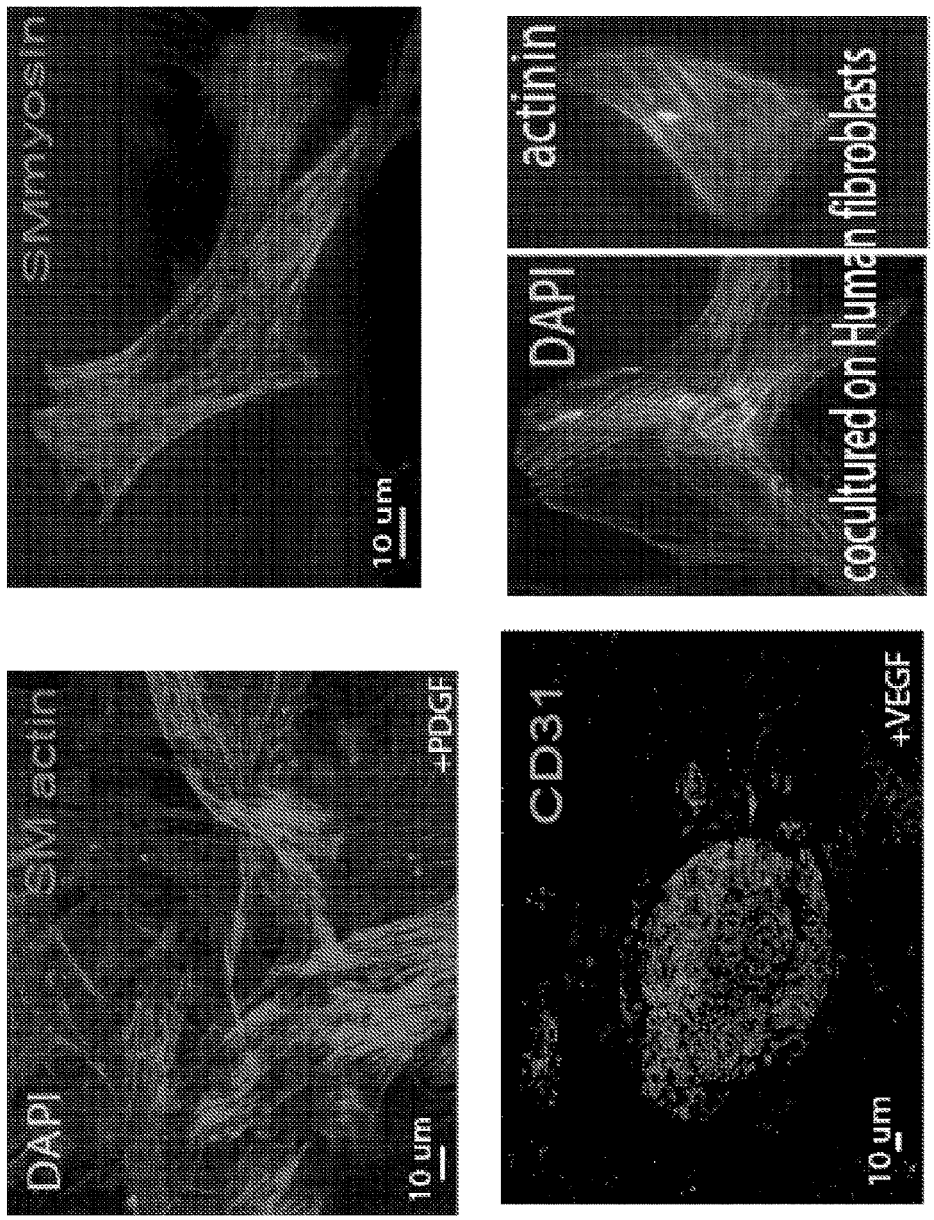
FIGURE 11B(continuing)

METHOD FOR GENERATING PRIMATE CARDIOVASCULAR PROGENITOR CELLS FOR CLINICAL USE FROM PRIMATE EMBRYONIC STEM CELLS OR EMBRYONIC-LIKE STATE CELLS, AND THEIR APPLICATIONS

The present invention is directed to a method for the in vitro preparation of cardiovascular progenitors cells from mammalian embryonic stem cells (ES cells) or mammalian embryonic-like state cells, preferably from primate, wherein said method comprises the use of the CD15 (SSEAI) marker as a positive cardiovascular progenitors differentiation marker. The present invention also claimed the use of a receptor tyrosine kinase inhibitor, particularly the SU5402 or SU11248 in association with the BMP2 for improving the efficiency of the desired differentiation. The present invention is also directed to the use of platelet lysate as foetal animal serum substitute in a culture medium intended to the proliferation or propagation of primate ES cells maintaining their pluripotency feature. Derived compositions or kits in relation with the claimed methods or product obtainable by the claimed methods form also part of the present invention.

Heart failure is becoming a predominant disease and a leading cause of death in most of developed countries. Regardless of the origin of myocardial failure (i.e, ischemic or genetic), the clinical symptoms result mainly from the death of cardiomyocytes replaced by a fibrotic and non contractile tissue. Pharmacological approaches to cure or relieve heart failure have been facing limitations. Because of a limited regeneration capability of the heart [1] and a shortage in donors for heart transplantation, an external source of cells has been envisioned as a therapeutic solution to bring a gain in function to diseased myocardium. For the last few years, hematopoietic stem cells had raised many hopes as a potential autologous cell source to repair diseased myocardium. However, the enthusiasm generated by the early non-controlled phase I studies has been dampened by the more recent recognition that out of four randomised controlled trials entailing intracoronary infusions of bone marrow-derived cells shortly after myocardial infarction, three failed to meet their primary end point, i.e., an improvement in left ventricular ejection fraction [2-5]. Combined with basic studies disproving the cardiogenic potential of these cells [6-7], the outcome of these trials demonstrates that these cells do not really regenerate the diseased myocardium and it is unlikely that their paracrine effects may be sufficient for restoring function of extensively scarred myocardium [8]. The same limitations apply to skeletal myoblasts [9]. Thus, these findings call for another stem cell source to achieve myocardial regeneration. Among various other cell types, embryonic stem (ES) cells [10-12] or ES cell-derived cardiomyocytes [13-14] have turned out to be the most promising for replacing scar fibrosis by new contractile elements. However, the number of cells required to regenerate a post-infarcted human myocardium (i.e., several hundreds of million) is too high to be reasonably achieved by in vitro engineering of ES cell-derived cardiomyocytes. For the last few years, we and others have shown that proliferative mouse ES cells engrafted in a diseased myocardium further differentiate into functional cardiomyocytes following in-vitro commitment using the cardiogenic morphogen BMP2 [10-12]. Cardiac-specified cells then complete their differentiation in response to the local cues present in the scar and do not generate any kind of tumors.

Primate Embryonic stem (ES) cells feature the capability to selfrenew and to differentiate in any cell lineage of the three embryonic layers namely the ectoderm, endoderm and mesoderm [35]. However, spontaneous differentiation of ES cells toward a specific cell lineage is poorly efficient, specifically for primate ES cells. Human ES cells do not share with mouse ES cells the same molecular mechanisms of self-renewal or capabilities of spontaneous differentiation [15]. For the last decade, laboratories have developed protocols to direct mouse and human ES (HES) cells toward their favourite cell type. These protocols are mandatory to: (i) better investigate and thus comprehend the genetic and epigenetic mechanisms underlying ES cell differentiation, (ii) use ES cells-derived differentiated cells as a toxicology model (iii) perform HTS (High Throughput Screening) aiming at discovering new cardiogenic molecules, markers of cardiac genetic diseases or new therapeutic drugs [36-37] (iv) design protocols of cell therapy of heart failure [38].

There is a clear need, therefore, to provide clinical grade cells which can subsequently differentiate into cardiomyocytes in situ following their transplantation in infarcted myocardium without any sign of hyperproliferation, by a method able to specifically differentiate in vitro a high number of primate ES cells or embryonic-like state cells toward a cardiovascular lineage.

In this context, it would be worthwhile to have further at one's disposal a simple and reproducible protocol to commit primate ES cells or embryonic-like state cells toward a cardiovascular lineage allowing to sort out the population of early cardiovascular progenitors which retain the capability to proliferate and repopulate the postinfarction scar.

This is the object of the present invention.

Herein, the inventors bring the proof of concept that primate ES cells such as Human ES cells or embryonic-like state cells, can also be directed toward a cardiogenic and vascular fate using the morphogen BMP2 in association with a receptor tyrosine kinase inhibitor and to selectively collect these cardiovascular progenitors thus obtained by using the positive CD15 (SSEA1) biomarker. Furthermore, the cells do differentiate into cardiomyocytes following engraftment into the myocardial scar without any sign of hyperproliferation. These data open the path for the use of early cardiovascular progenitors, which retain the capability to proliferate and repopulate the postinfarction scar.

Thus, the present invention relates to methods for obtaining substantially pure populations of primate cardiovascular progenitors as well as compositions such as therapeutical composition, containing these cell populations and method of using these cell populations.

In a first aspect, the invention is directed to an in vitro method for the preparation of cardiovascular progenitors cells from mammalian ES cells or from mammalian embryonic-like state cells, preferably for the preparation of a substantially purified population of cardiovascular progenitors, wherein said method comprises the following step of:

a) culturing of mammalian ES cells or embryonic-like state cells in a medium containing suitable agents allowing their proliferation and maintaining their pluripotency;

b) differentiating the mammalian pluripotent ES cells or embryonic-like state cells obtained in step a) toward cardiovascular progenitors cells by suspending said pluripotent ES cells or embryonic-like state cells in a medium containing BMP2 (Bone Morphogenetic Protein 2); and c) selecting and collecting the differentiated mammalian ES cells or mammalian embryonic-like state cells obtained in step b) which display the CD15 marker at their membrane surface, the mammalian ES cells or embryonic-like state cells displaying said CD15 marker being selecting and collecting as cardiovascular progenitors cells.

In a preferred embodiment, said embryonic-like state cells are induced pluripotent stem cells, commonly abbreviated as iPS cells, preferably from adult somatic cells, particularly from adult fibroblast.

In a more preferred embodiment, said iPS cells are obtained using human dermal fibroblasts infected by lentivirus harbouring the cDNAs encoding Oct4, Sox2, Lin 28, Klf4 and Nanog, preferably under ES cells culture conditions [49].

By "pluripotency", it is intended to designate herein pluripotent ES cells-derived cells that are the descendants of totipotent embryonic stem cells and can differentiate into cells derived from any of the three germ layers ectoderm, endoderm and mesoderm.

By iPS cells, it is intended to designate pluripotent stem cell artificially derived from a non-pluripotent cell, typically an adult somatic cell, by inducing expression of certain genes.

The preparation of iPS cells from mammalian cells, particularly from mouse cells or from human cells is well known from the skilled person. [46-49].

In a preferred embodiment, the invention is directed to an in vitro method according to the present invention wherein said mammalian cells are primate, mouse or rat cells, preferably primate cells and more preferably human cells.

Primate embryonic stem cells can be isolated from blastocysts of members of the primate species (see for example U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al., Nature Biotech., 18:399, 2000.

Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Tissue culture supplies and reagents are available from commercial vendors such as Gibco/BRL, Nalgene-Nunc International, Sigma Chemical Co., and ICN Biomedicals.

In a preferred embodiment, said BMP2 protein (also named BMP-2) is the human BMP2, more preferably a recombinant hBMP2, more preferably the human BMP2 protein having the amino acids sequence depicted in GenBank Accession Number AAF21646.

In a preferred embodiment, the CD-15 marker is the human CD-15 (also named "SSEA1" marker, "SSEA1" for "Stage Specific Embryonic Antigen 1").

Angiogenic growth factors such as fibroblast growth factors (FGFs) and vascular endothelial growth factors (VEGFs) are currently targets of intense efforts to inhibit deregulated blood vessel formation in diseases such as cancer. FGFs and VEGFs exert their effects via specific binding to cell surface-expressed receptors equipped with tyrosine kinase activity. Activation of the receptor kinase activity allows coupling to downstream signal transduction pathways that regulate proliferation, migration and differentiation of endothelial cells. Inhibitors of tyrosine kinase activity such as the tyrosine kinase activity of FGF and/or VGR receptor are currently in clinical trials.

The inventors have surprisingly demonstrated that such receptor tyrosine kinase (RTK) inhibitor, particularly FGFR inhibitor or multitargeted tyrosine kinase receptor inhibitors, particularly resulting to the inhibition of the tyrosine kinase activity of the VEGF receptor (R-1 and/or R-2), and/or fetal liver tyrosine kinase receptor 3 (FLT3), and/or KIT (stem-cell factor [SCF] receptor), and/or PDGFRα, and/or PDGFRβ, can be used in step b) to improve, likely by a synergic effect with BMP2, the differentiation of primate ES cells or embryonic-like state cells in cardiovascular progenitors cells.

In a preferred embodiment, the RTK inhibitor is selected from the group consisting of SU5402 and SU11248.

The SU5402 compound has the following formula:
3-[3-(2-Carboxyethyl)-4-methylpyrrol-2-methylidenyl]-2-indolinone.

SU5402 inhibits the tyrosine kinase activity of fibroblast growth factor receptor 1 (FGFR1); (IC50=10-20 µM in the presence of 1 mM ATP). It also inhibits aFGF-induced tyrosine phosphorylation of ERK1 and ERK2 (IC50=10-20 µM). SU5402 is considered as only a weak inhibitor of tyrosine phosphorylation of the PDGF receptor and does not inhibit phosphorylation of the insulin receptor. It does not inhibit the kinase activity of the EGF receptor (Mohammadi M. et al., 1997, Science 276, 955).

The SU11248 compound (also referenced as "Sunitinib malate" or Sutent" has the following formula:
N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide.

Sunitinib (sunitinib malate; SU11248; SUTENT; Pfizer Inc, New York, N.Y.) is a multitargeted RTK inhibitor with antitumor and antiangiogenic activities. Sunitinib has been identified as a potent inhibitor of VEGFR-1, VEGFR-2, fetal liver tyrosine kinase receptor 3 (FLT3), KIT (stem-cell factor [SCF] receptor), PDGFR, and PDGFRβ in both biochemical and cellular assays (Faivre et al., Journal of Clinical Oncology, Vol. 24, N° 1, 2006: pp. 25-35).

When the SU5402 compound is used as FGF inhibitor in step b), it is preferred that the primate ES cells or embryonic-like state cells, particularly the human ES cells (HES) or human embryonic-like state cells were treated in step b) for respectively 48 hrs and 6 days with a BMP2 concentration of 10 ng/ml medium (±5 ng/ml) in the presence of 1 µM SU5402 (±0.5 µM). Following the 6 days treatment with 10 ng/ml BMP2 and 1 uM SU5402, the embryonic-like state cells (iPS cells) can be trypsinised.

One of the problems which have to be solved in this context, when production of therapeutical cells is wished to commit primate ES cells or primate embryonic-like state cells toward a cardiac lineage, is to have further at one's disposal compounds used in the production method, such as RTK inhibitor, which have been already used as therapeutical compound. Indeed, these compounds are known not to have relevant side-effects and generally, available as clinical grade compound.

After demonstrating the synergic effect of FGF inhibitor in step b) for differentiating the primate ES cells or primate embryonic-like state cells in cardiac progenitor cells (or early cardiovascular progenitors cells having the capability to proliferate and repopulate the postinfarction scar after administration to the patient), the inventors have demonstrated surprisingly that it will be possible to use a multitargeted RTK inhibitor available as clinical grade, such as the SU11248, as synergic compound in step b) in place of the FGF inhibitor.

Preferably, when a multitargeted RTK inhibitor, such as SU11248, is used in place of a FGF inhibitor, it is preferred that the primate ES cells or primate embryonic-like state cells, particularly from human, were treated with about 5 times more quantity of such in step b) for 48 hrs with a BMP2 concentration of 10 ng/ml medium (±5 ng/ml) in the presence of 5 µM SU (±2 µM).

In a preferred embodiment the invention provides a method for preparing a substantially pure population of progenitor cells which is at least about 80%, preferably 85%, 90%, 95%, 97%, 98% and 99% pure cardiac progenitor cells which display at their surface the marker CD-15 and, preferably, which retain their capability to proliferate and repopulate the postinfarction scar after administration to a patient.

In step a) of the method according to the invention, medium for culturing primate ES cells or primate embryonic-like state cells allowing their proliferation and maintaining their pluripotency are well known by the skilled person.

Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Tissue culture supplies and reagents are available from commercial vendors such as Gibco/BRL, Nalgene-Nunc International, Sigma Chemical Co., and ICN Biomedicals.

For example, it is known that primate ES cells required feeder cells for their culture, such as mouse embryonic fibroblasts, and FGF2 (bFGF) to maintain their pluripotency.

By "Feeder cells" it is intended to designate cells that are co-cultured with the primate ES cells. They provide an environment in which the primate ES cells type can grow. The culture of the primate ES cells can be supported by primary mouse embryonic fibroblasts (MEF) or primary human foreskin fibroblasts as exemplified. Immortalized mouse embryonic fibroblasts or human foreskin fibroblasts cells can also be used as feeder cells.

For example of basic medium which can be used for culturing primate ES cells or primate embryonic-like state cells, the KO™-DMEM medium from Invitrogen (or from Gibco, Rockville, Md., USA) can be cited.

It is preferred that FGF2 (fibroblast growth factor 2, also named bFGF) is added to the basic medium after a period of at least an overnight with ES cell or embryonic-like state cells basic medium without FGF2 on feeder cell layer.

It is preferred that the culture medium is changed every day.

Generally, the cell colonies are dissociated into single cells or small cell clusters every 4-5 days using trypsin or collagenase depending on the primate ES cells or primate embryonic-like state cells source (monkey or human source).

It is preferred to never let the ES cells or primate embryonic-like state cells colonies reaching confluency in the dish.

In step a) of the method according to the invention, the medium for culturing primate ES or primate embryonic-like state cells comprised a basic medium, such as the KO™-DMEM medium, supplemented with platelet lysate obtained from primate blood, preferably from human blood.

Preferably, the platelet lysate is a total human freeze-thawed platelet lysate, more preferably at a concentration range of 5% to 15% (V/V), the most preferred at a concentration of 7.5% (V/V)±2.5% in the basic medium.

The inventors have demonstrated that the use of platelet lysate in place of the FBS (foetal bovine serum) content usually present in the basic medium at this stage of a culture of primate ES cells or primate embryonic-like state cells allows to obtain the proliferation of non-differentiated primate ES cells or primate embryonic-like state cells, the use of such platelet lysate allowing the maintain of the pluripotency of the primate ES cells or primate embryonic-like state cells obtained after this step of proliferation or propagation.

One of the benefit of platelet lysate used in place of FBS is to eliminate the problem of possible contamination of FBS with infectious microorganism, virus or prion and thus to produce therapeutical cells composition with a better safety.

The blood platelet lysate can wholly or partly replace foetal bovine serum in cell culture.

To obtain such a platelet lysate, the whole blood is for example separated into red blood corpuscles and platelet-rich plasma by centrifugation suitably at about +4° C.

Subsequently the platelet-rich plasma can be concentrated by ultrafiltration, after which the concentrated platelet-rich plasma is optionally frozen for storage and/or analysis and further lysis of the platelets included. After optional freezing, the frozen plasma is thawed, preferably at a temperature below 37° C., more preferred below 20° C.

After or before thawing of the concentrated platelet-rich plasma, water can be added for accelerate the total lysis of the platelets included if necessary.

The PRP may use the patient's own plasma and/or platelets who will receive the therapeutical cells. The platelets may be present in the plasma or PRP at a range of from about 200,000 to 2,000,000 platelets per cubic centimeter, or more. The PRP may be obtained using autologous but also allogenic, or pooled sources of platelets and/or plasma from a variety of primate sources, including human sources.

In step b) of the method according to the invention, the basic medium for differentiating primate ES cells or primate embryonic-like state cells can be selected for example in the group consisting of RPMI or DMEM medium.

In a preferred embodiment, the primate stem cells or embryonic-like state cells, can be treated for respectively 96 H and 6 days with 10 ng/ml BMP2 in RPMI supplemented with 2% B27, and: 1 μM SU5402 (research grade) or 5 μM SU11548, SUTENT (clinical grade).

It is preferred that the cells do not reach confluency at the end of BMP2 treatment. It is also preferred that BMP2 is added as soon as small colonies of ES cells appear.

The invention also includes a substantially purified population of cardiac progenitor cells susceptible to be obtained by the method of the present invention, wherein the cardiac progenitor cells display at their membrane surface the CD15 marker and, preferably retain their capability to proliferate and repopulate the postinfarction scar when administrate to a patient in need thereof.

In certain embodiment, the cells of the cardiac progenitor cells population according to the present invention express the early mesodermal Brachyury and Tbx6 markers, the cardiac Tbx20 and Mef2c markers, the GATA4, NRx2.5, Isl1, Tbx18 markers and the Oct-4A marker.

Preferably, by substantially purified population is meant that greater than about 80% of the cells are cardiac progenitor cells, preferably greater than about 90%, more preferably greater than about 95%, more preferably yet greater than about 98% and most preferably greater than about 99%.

The substantially purified population of cardiac progenitor cells of this invention is useful for many clinical applications, preferably as a therapeutical composition or a medicament.

The invention particularly concerns the use of the purified population of primate cardiac progenitor cells of this invention, preferably a population of human cells, for preparing a therapeutic composition for replacing or regenerating cells or tissues in a primate, particularly cardiac cells. In particular, the invention concerns the use of a population of human cardiac progenitor cells of this invention differentiated from human embryonic stem cells for treating heart failure in a human.

The invention further comprised a method for selectively separating cardiac progenitor cells from a primate cells population containing non-differentiated (pluripotency) ES cells or (non-differentiated) embryonic-like state cells and cardiac progenitor cells, or a method for enriching a primate cells population cell in cardiac progenitor cells wherein said method comprises the following steps of:

A) contacting the cells population with anti-CD15 antibodies; and

B) selecting the cells that bind specifically to the CD15 antibodies or eliminating the cells which are not bound the anti-CD15 antibodies, said cells having the capability to specifically recognize and to bind the CD15 antibodies being the primate cardiac progenitor cells which are desired to be kept in the cells population.

Preferably, in step A), the anti-CD15 antibodies are anti-human CD15 antibodies, most preferably, monoclonal antibodies.

In a preferred embodiment, the anti-CD15 antibodies are labelled, more preferably with a marker which can be used to select and to separate the cells displaying the CD15 marker from a cells population, preferably from a cells population obtained or susceptible to be obtained by the steps a) and b) of the method for the preparation of a population of cardiovascular progenitors cells from primate ES cells or embryonic-like state cells according to the present invention.

More preferably, said antibody marker is a fluorescent marker such as FITC.

In another preferred embodiment, the anti-CD15 antibodies are bound at the surface of magnetic beads or articles or coupled to magnetic compounds.

Method using magnetic beads or particles is usually implemented for sorting cells. Antibodies specific for a particular cell of interest are covalently bond to magnetic particles. They then incubate a mixture of cells in a solution with the magnetic antibodies. The entire reaction mixture is exposed to a magnetic field, which retains the cells of interest. Some of these particles are even composed of materials that naturally degrade without adversely affecting cell function. Such a system to separate or enrich population in specific cell is well known from the skilled man (see BD Biosciences system, (San Jose, Calif. USA); positive cells selection with the Midi-MACS™ separation system from Miltenyi Biotech (Bergisch Gladbach, Germany), Polysciences or Dynal Biotech)).

As alternatives in cell separation, the well established fluorescence-activated cells sorting (FACS) technique can be also used (Flow cytometers can measure and separate up to 500,000 cells per minute).

The invention further includes a kit useful for enriching for cardiac progenitor cells from a cells population containing non-differentiated primate ES cells or (non-differentiated) embryonic-like state cells, and cardiac progenitor cells. The kit includes anti-CD15 antibodies, preferably anti-human CD15 antibodies.

Preferably, monoclonal antibodies are used.

Preferably, the anti-CD15 antibodies are labelled, more preferably with a marker which can be used to select and to separate cells displaying the CD15 marker from a cells population, preferably from a cells population obtained or susceptible to be obtained by the steps a) and b) of the method according to the present invention.

More preferably, said antibody marker is a fluorescent marker such as FITC.

In another preferred embodiment, the ant-CD15 antibodies are bound at the surface of magnetic beads or coupled to magnetic compounds.

Preferably, instructions are provided which have information to the user regarding the use of the antibodies for enriching for cardiac progenitor cells from the cells population.

In certain embodiments, the kit also contains magnetic beads, e.g., superparamagnetic microparticles. The magnetic beads can be complexed to the anti-CD15 antibodies, or they can be separate. The kit also can include an electromagnet for use in generating a magnetic field.

In another aspect, the present invention is directed to a method for proliferating or propagating primate ES cells or embryonic-like state cells, particularly human cells, maintaining their pluripotency feature during this step of proliferation or propagation, said primate ES cells or embryonic-like state cells being usually cultivated in a medium supplemented with foetal mammal serum, such as FBS, characterized in that said foetal serum is replaced by a platelet lysate from a primate, preferably a human platelet lysate, preferably at a concentration of 7.5% (V/V)±2.5%.

A composition or a culture medium used for culturing cells, preferably primate ES cells, comprising BMP2 and a RTK inhibitor.

Preferably the RTK inhibitor is a FGF inhibitor or a multitargeted RTK inhibitor capable to inhibit VEGFR, FLT3, KIT and/or PDGFR.

More preferably, the RTK inhibitor is selected from the group consisting of SU5402 and SU11248.

Preferably, the composition or the medium contains 10 ng/ml BMP2 (±5 ng/ml) for 1 µM SU5402 (±0.2 µM).

Preferably, the composition or the medium contains 10 ng/ml BMP2 (±5 ng/ml) for 5 µM SU11248 (±2 µM).

Other features and advantages of the invention will be apparent from the following detailed description, and from the claims.

LEGENDS OF THE FIGURES

FIG. 1: Beating activity of I6 HES cells-derived EBS at day 30. Cells are treated for 48 H with BMP2 prior to the generation of EBs. AN EB is scored as positive if it features at least three beating areas. Data are expressed as mean (blue bars) ±SEM (pink bars) (n=3 experiments).

Figure 2:
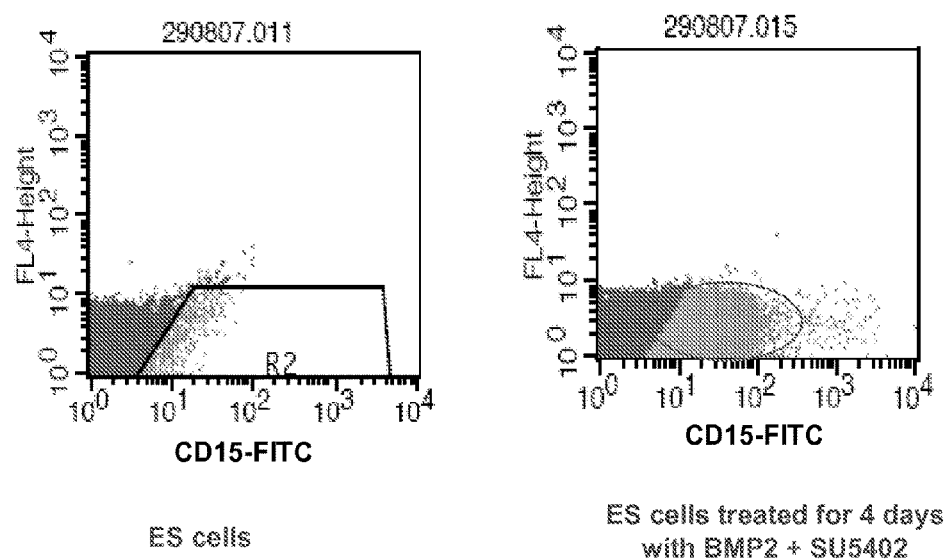

FIG. 2: FACS analysis of CD15 positive cells. Cells are treated for 4 days with BMP2 and SU5402 in RPMI/B27 medium. Cells are then washed once with D-PBS, incubated for 3 min with trypsin. Cells are spun down and resuspended in D-PBS supplemented with 3% Foetal calf serum containing the anti-CD15-FITC antibody used at a dilution of 1/100. Cells are incubated for 30 min at 4° C. before FACS monitoring. The figure is representative of 3 experiments using HUES-24 or ORMES cell lines. Data are expressed as mean±SEM.

FIGS. 3A, 3B, 3C and 3D: Gene expression profile of CD15-positive cardiovascular progenitors.

Figure 3A:
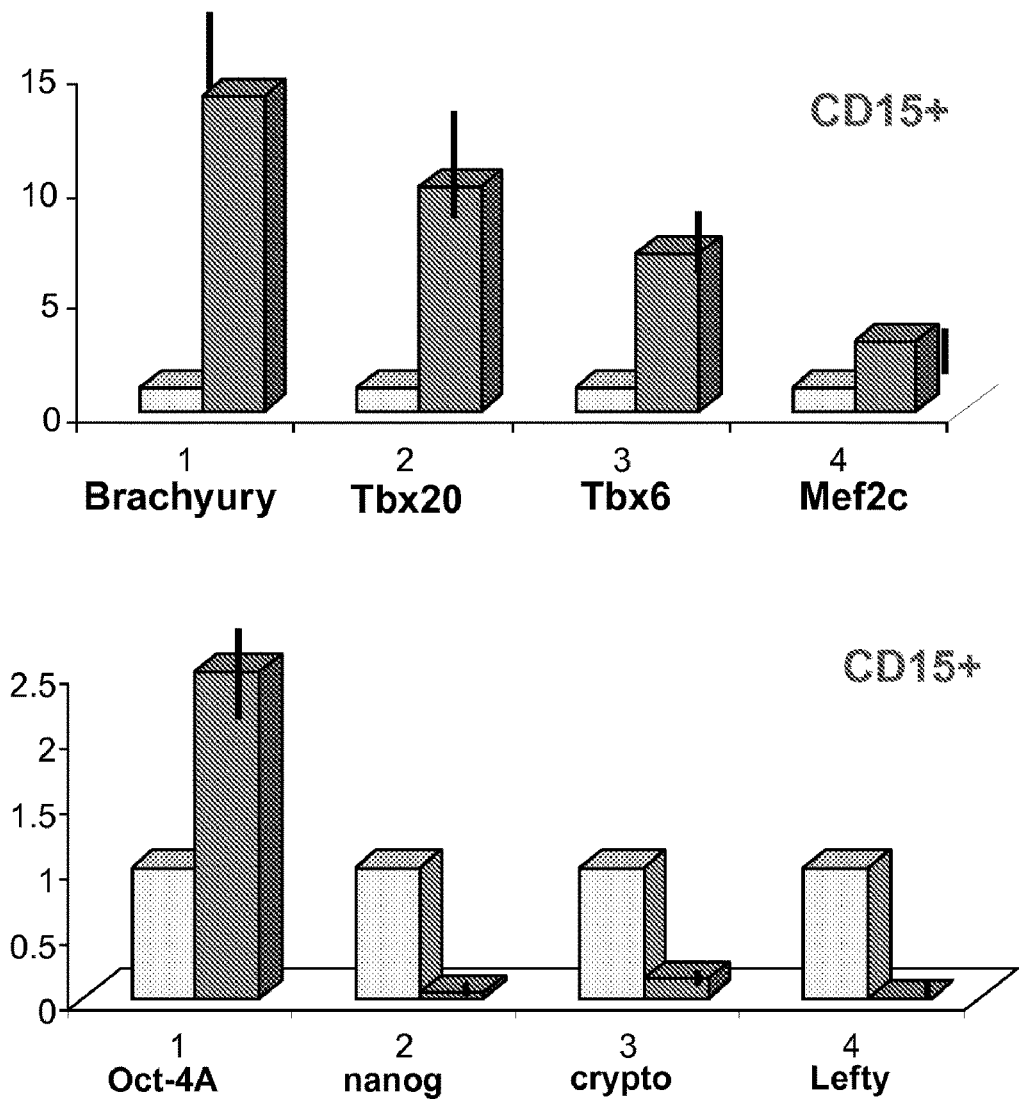
Figure 3B:
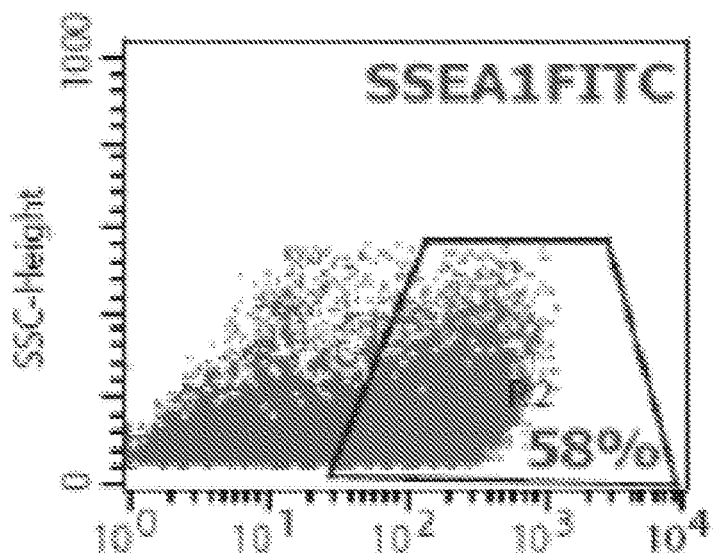

After sorting out the CD15-positive primate ES cells using the MACS system, cells are lysed and RNA extracted. Gene expression is monitored by real time quantitative PCR. The FIG. 3A is representative of 3 experiments using HUES-24 or ORMES cell lines. Data are expressed as mean±SEM and normalised to the CD15– cell population.

Figure 3C:
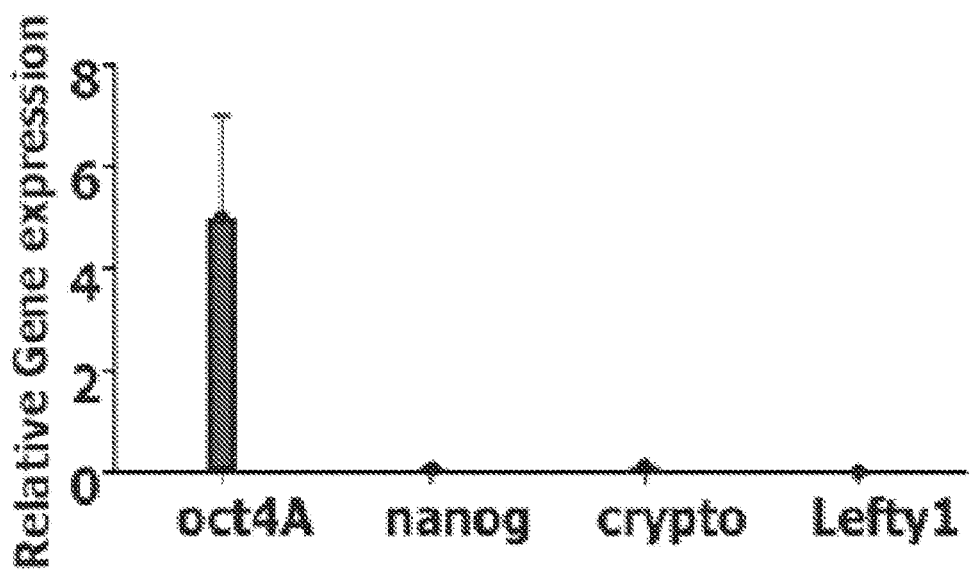
Figure 3D:
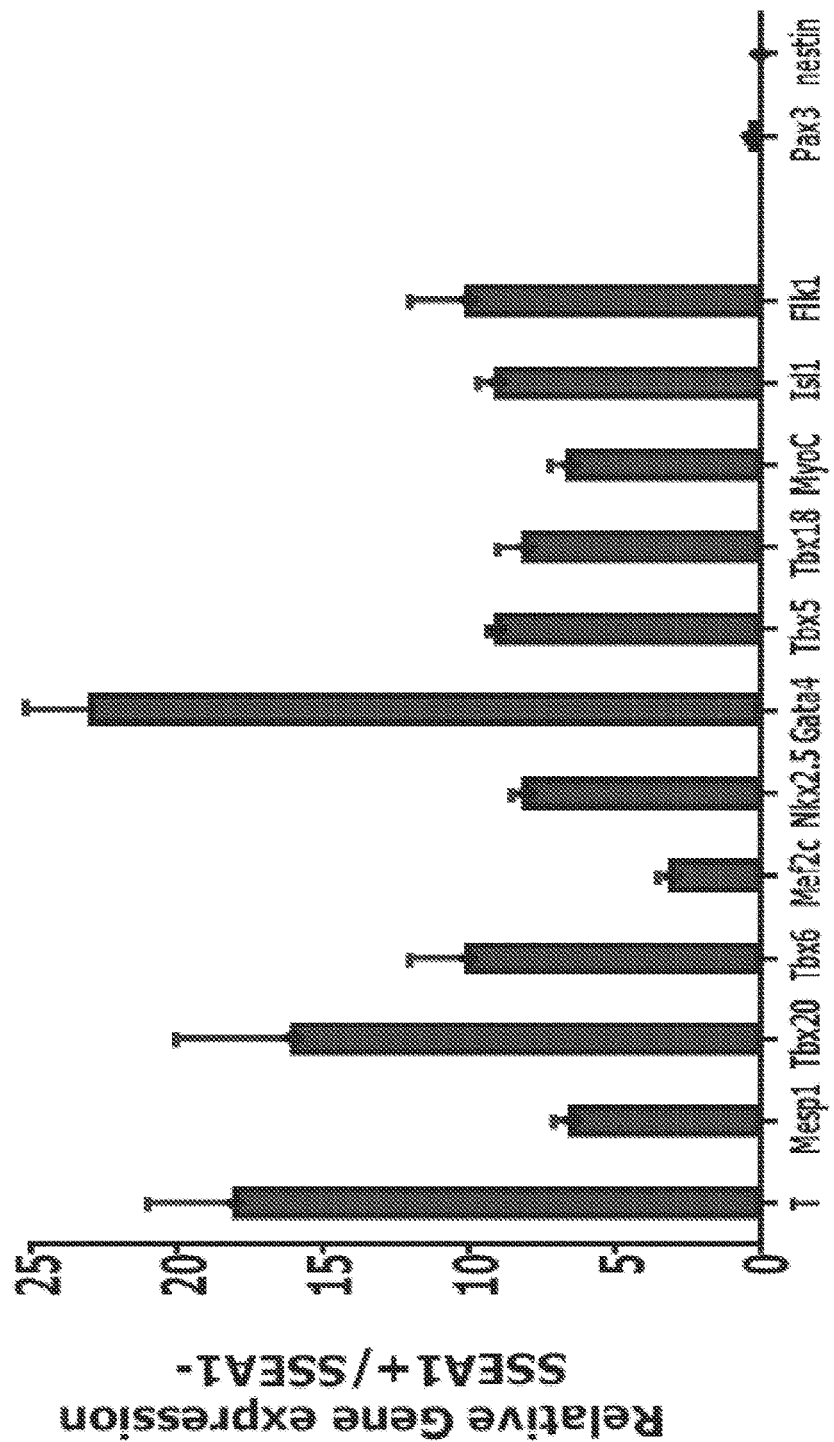

After sorting out the CD15-positive primate ES cells using the MACS system following checking expression of CD15 by FACS (FIG. 3B), cells are lysed and RNA extracted. Gene expression is monitored by real time quantitative PCR. The FIGS. 3C and 3D are representative of 5 experiments using HUES-24, 16, HUES-9 or ORMES cell lines. Data are expressed as mean±SEM and normalised to the CD15– cell population.

Figure 4A:
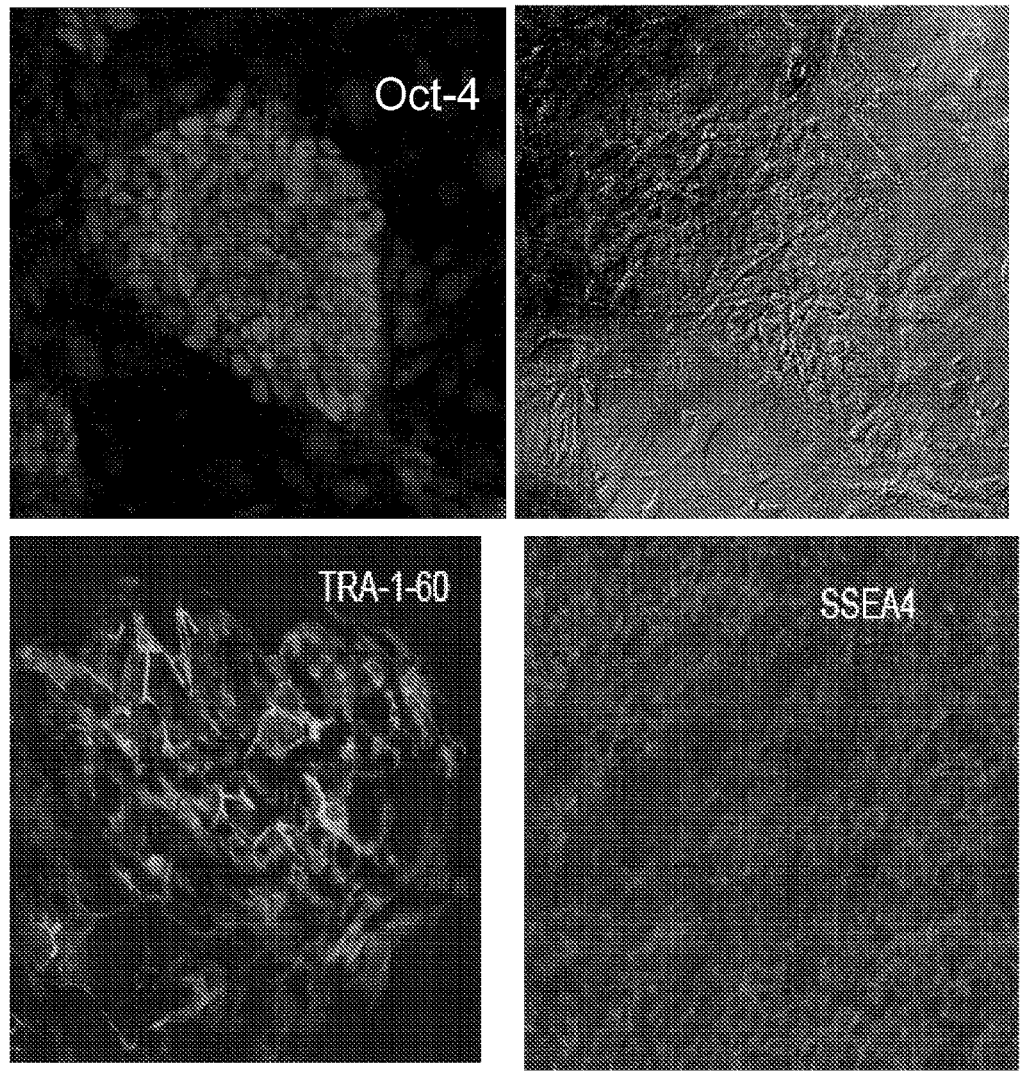
Figure 4B:
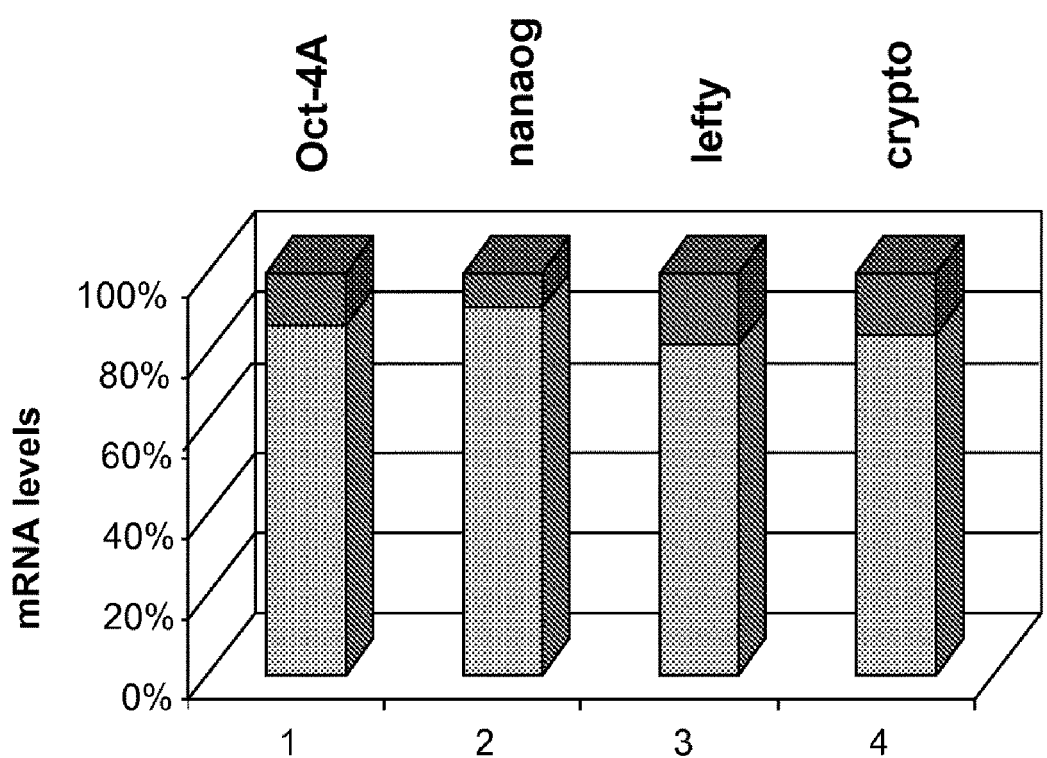

FIGS. 4A and 4B: FIG. 4A: Immunofluorescence of HUES cells cultured for 10 passages in clinical grade medium. The antibodies used are: anti Oct-4, TRA-1-60 and SSEA-4. FIG. 4B: Real time PCR monitoring of pluripotency genes expression in HUES cells cultured for 10 passages in clinical grade medium.

Figure 5:
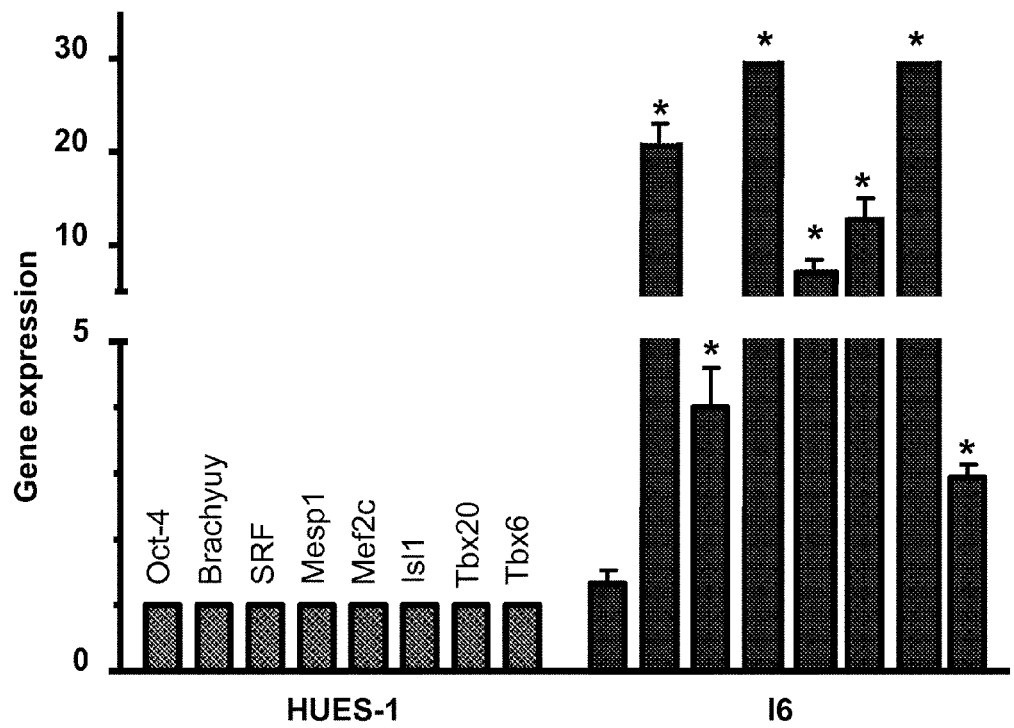

FIG. 5: Comparison of mesodermal and cardiac gene expression in HUES-1 and I6 cells. RNA was extracted and reverse transcribed from undifferentiated HUES-1 (passages 22-25) and I6 cell lines (passages 27-32) cultured for at least 5 passages after thaw-out on MEF prior to stimulation with BMP2. Differentiated colonies were cut out the plate before RNA extraction. Gene expression was estimated by real-time PCR and expressed as a ratio between expression in I6 and expression in HUES-1. Data are normalised to β-tubulin expression and expressed as means±SEM (n=3). * Statistically significant ($p \leq 0.01$).

Figure 6A:
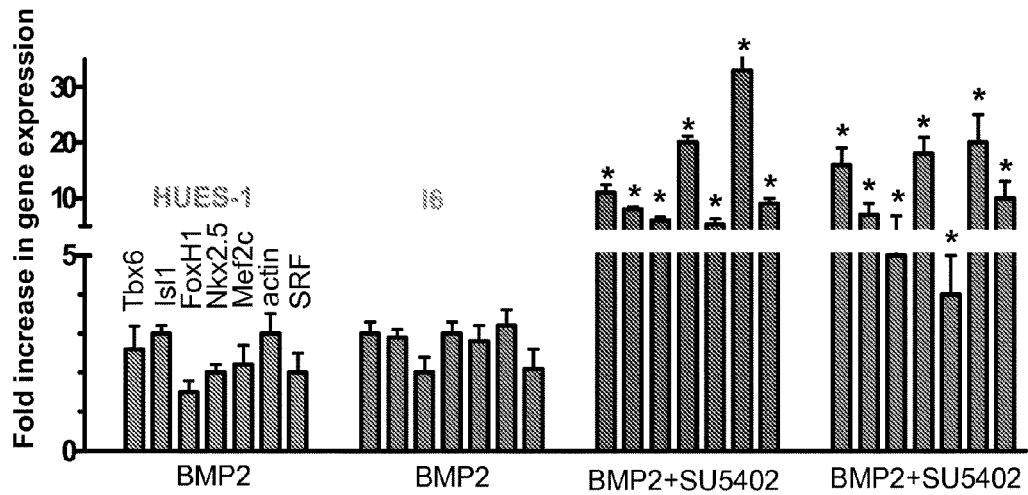
Figure 6B:
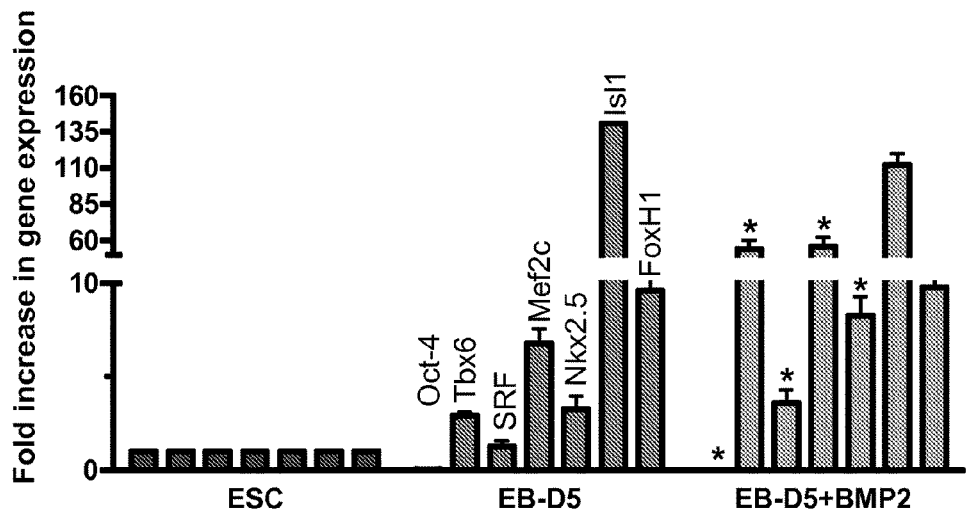

FIGS. 6A and 6B: FIG. 6A: HUES-1 and I6 cells were treated for 48 hrs with 10 ng/ml BMP2 in the presence or absence or FGF inhibitor SU5402 and RNA extracted and reverse transcribed. Gene expression was monitored by real-time quantitative PCR. Results are expressed as fold stimulation in gene expression when compared to untreated ES cells. FIG. 6B: HUES-1 cells treated or not with BMP2 and SU5402 were allowed to aggregate to form embryoid bodies (EB). EBs were kept in suspension for 5 days before RNA extraction and real time PCR. Data are normalised to β-tubulin expression and expressed as means±SEM (n=3-5). * Statistically significant ($p \leq 0.01$).

Figure 7:
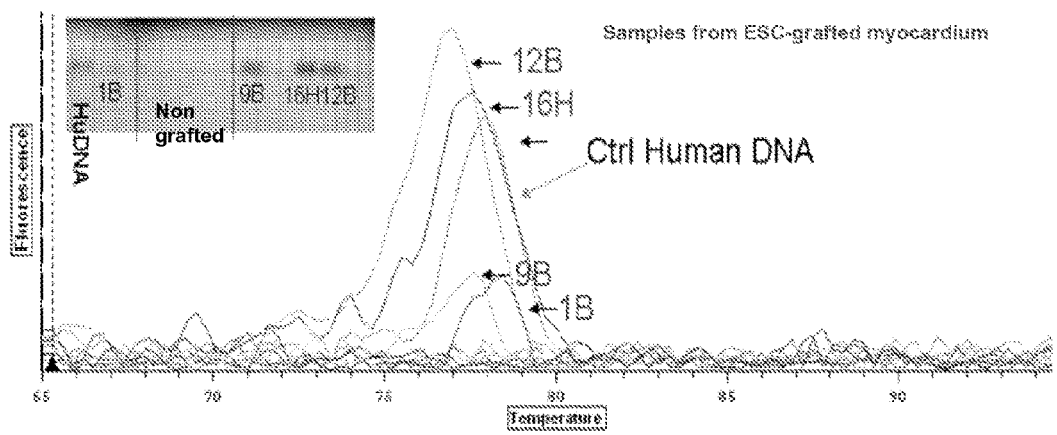

FIG. 7: BMP2-treated HES cells were engrafted into post-myocardial infarcted rats and their fate was examined two months later by real time PCR of α-actin mRNA following reverse transcription of mRNA extracted from myocardial sections. The figure shows both the profile of the melting curves of amplicons and the amplicons on gel. Human RNA was used as a positive control. * Statistically significant ($p \leq 0.01$).

Figure 8A:
Figure 8B:
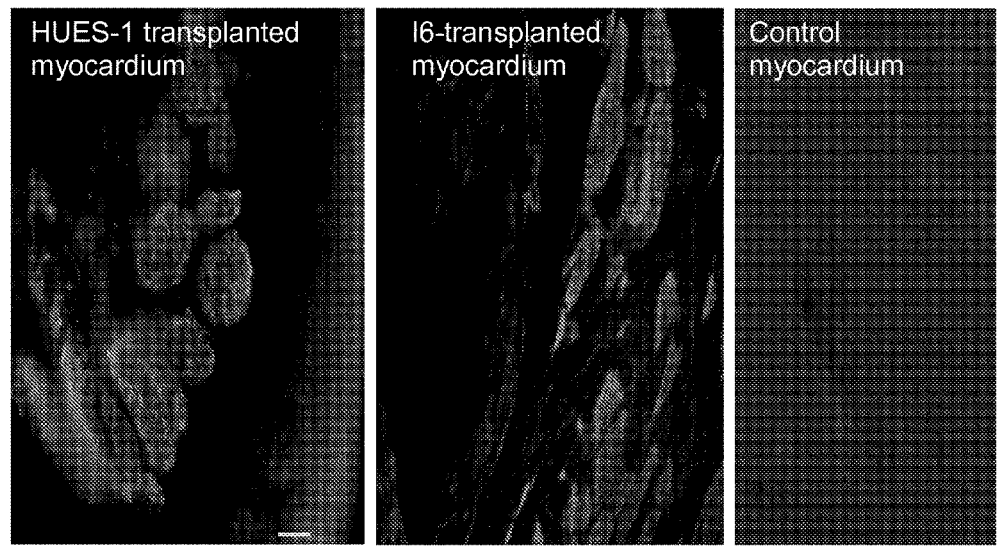
Figure 8C:
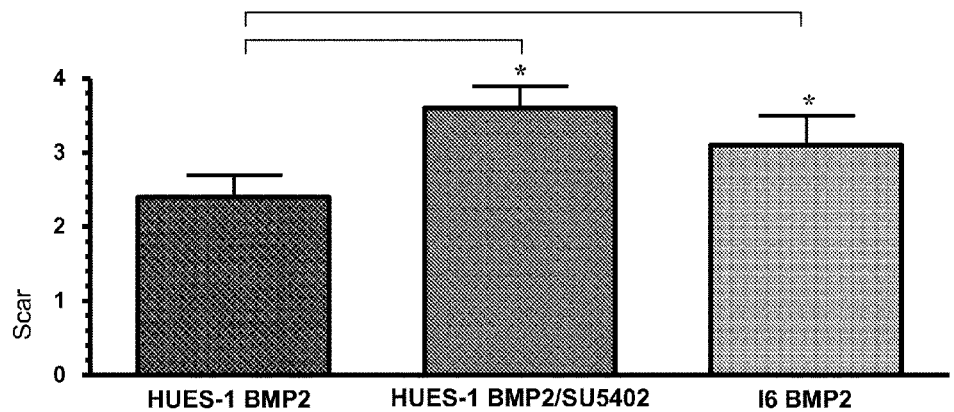

FIGS. 8A, 8B, 8C and 8D: Immunostaining of cryosections from HES cell-engrafted myocardium using an antihuman lamin antibody (FIG. 8A) (note that the anti-lamin antibody stained HES-derived cells within the scar area but not the surrounding endogenous rat cells) and an anti-human β-myosin antibody (FIG. 8B). The antibody did not recognize the adult rat endogenous β-MHC (left panel B) while it bound human β-MHC. Images were acquired in confocal microscopy. (FIG. 8C) quantification (in %) of the human β-MHC positive regions in the scars of myocardium engrafted with BMP2- or BMP2 with SU5402-treated HUES-1 or BMP2-treated I6 cell lines: * Statistically significant ($p \leq 0.025$). The area of β-MHC positive area within the scar was calculated using the threshold function of Metamorph software (FIG. 8D) a transversal section stained by the anti-β myosin antibody revealed some sarcomeric structures. The size was calculated using the scaling system of the ZEISS software driving the confocal microscope.

Figure 9:
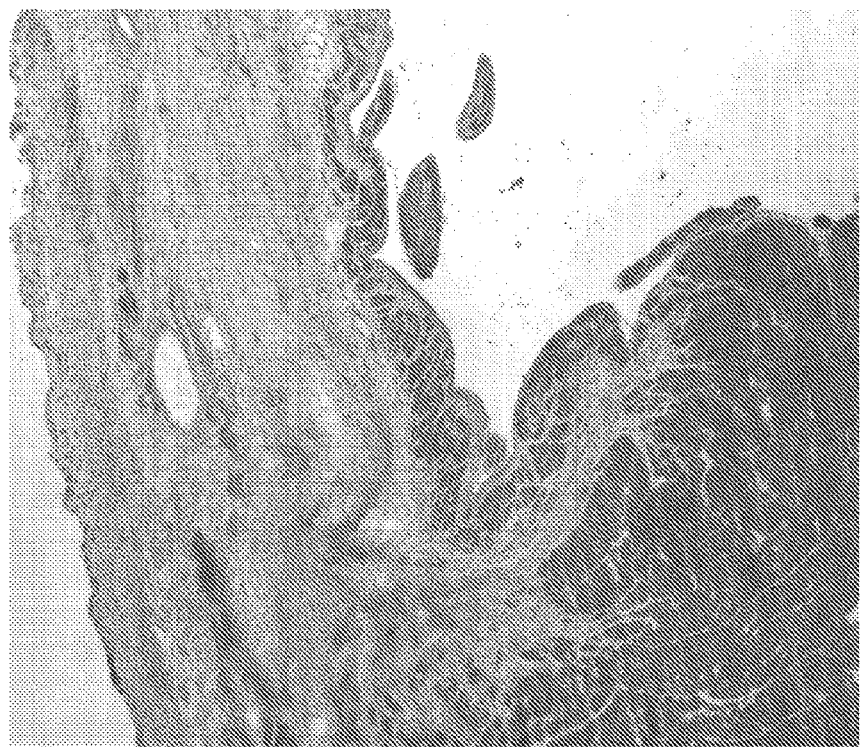

FIG. 9: Eosin-Hematoxylin stained section from HES cell-engrafted myocardium. The scar area does not show any sign of cell infiltration of cell proliferation.

Figure 10A:
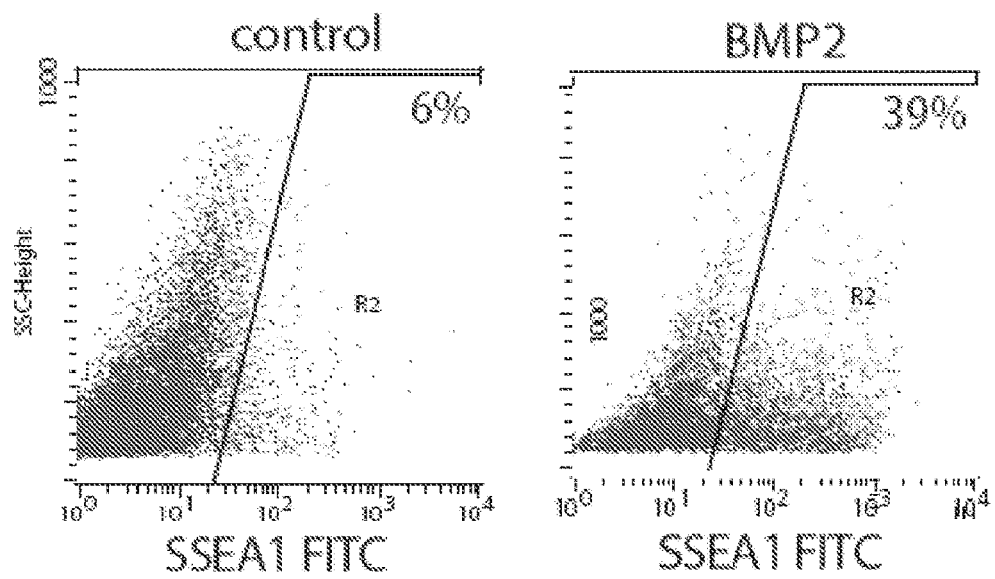
Figure 10B:
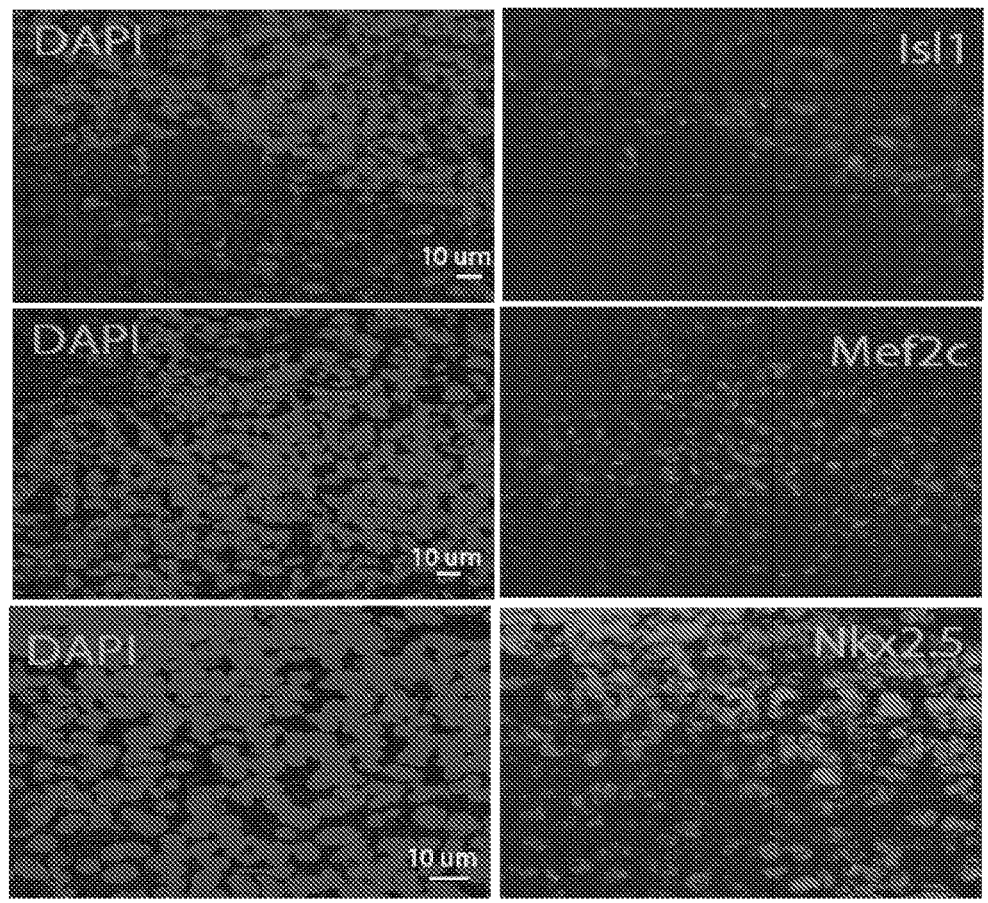
Figure 10B:
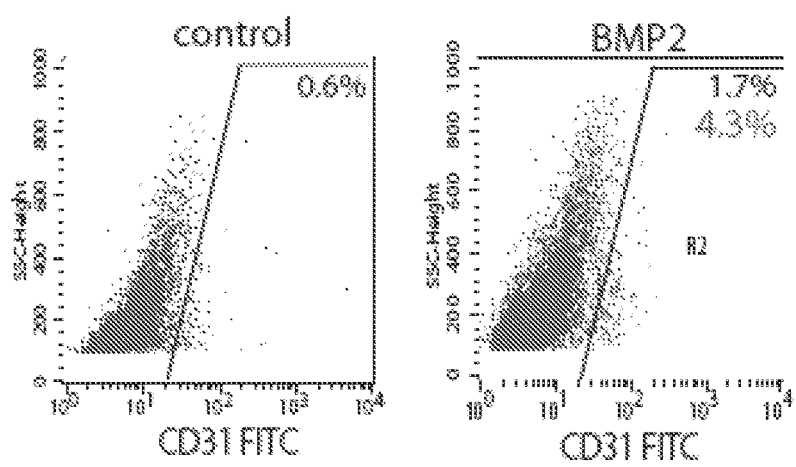

FIGS. 10A and 10B: IPS cells give rise to CD15+ cardiovascular progenitors, CD15+ iPS cells were generated and sorted following 6 days BMP2 treatment FIG. 10A: FACS analysis of cardiac markers in CD15+ cells.

FIG. 10B: Immunofluorescence of CD15+ cells cultured for 5 days on MEF. The scale bar indicates 10 µm.

Figure 11C:
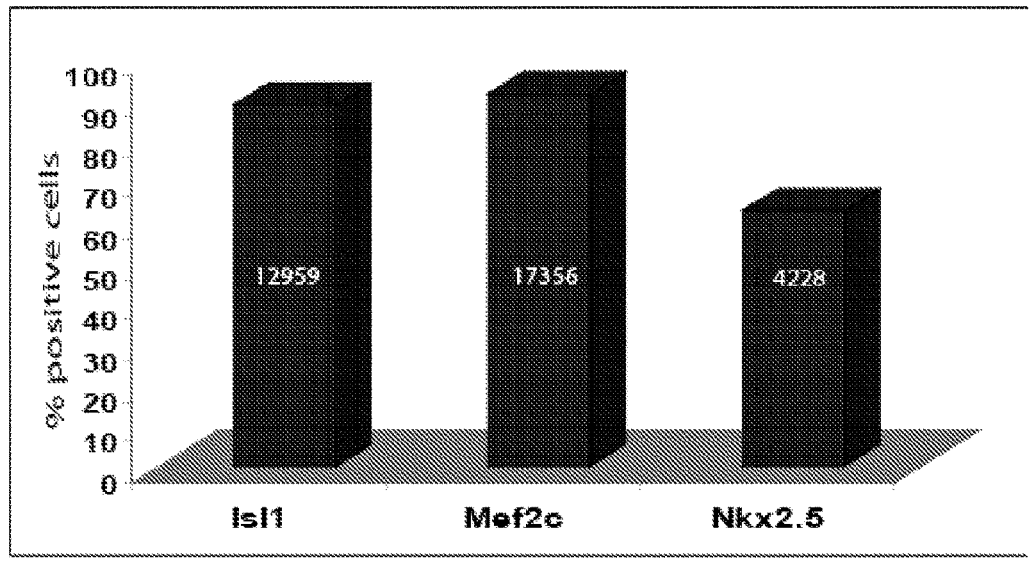
Figure 11C:
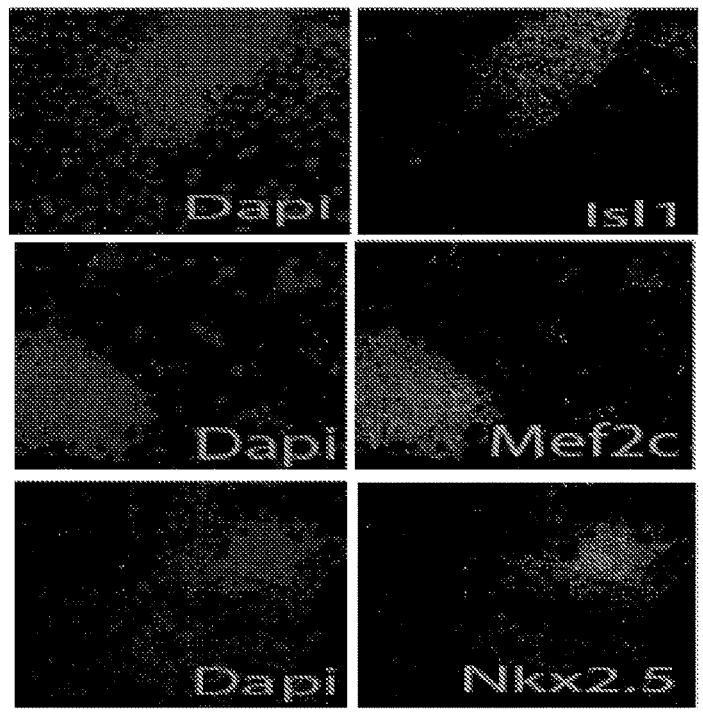

FIGS. 11A, 11B and 11C: CD15+ cells express cardiac, endothelial and vascular proteins markers; CD15+ sorted cells were cultured for 5 days on MEF and immunostained with the indicated markers; some cells were treated with VEGF or PDGF and immunostained with anti smooth muscle actin and myosin or CD31. Some others were cultured with human fibroblast isolated from the myocardium and stained with an anti-actinin antibody.

MATERIALS AND METHODS FOR EXAMPLES 1-3

Knockout™-DMEM (Invitrogen cat n° 10829018)
Knockout™ SR serum replacement (cat n° 10828028 Invitrogen) test batch before using:
Trypsin 0.05%/0.5 mM EDTA4Na 1× (Invitrogen cat n° 25300054)
Glutamax 200 mM (Invitrogen cat n° 35050038)
MEM Non essential Amino Acids solution (200 mM) (Invitrogen cat n° 11140035)
Mercaptoethanol (Invitrogen cat n° 31350010) (make solution at $10^{-7}$ M in PBS and use for one month)
RPMI 1640 with glutamax (Invitrogen cat n° 61870-010)
F12 nutrient supplement with glutamine (Invitrogen cat n° 21765-029)
Dulbecco Phosphate Buffered Saline (D-PBS) Ca- and Mg-free (Invitrogen cat n° 14200067)
B27 50× supplement without vitamin A (Invitrogen cat n° 12587010)
Gelatin 2% solution from bovine skin cell (Invitrogen cat n° G1393-100 ml)
Mitomycin 2 mg Sigma cat n° M4287)
FGF2 (Human recombinant, preprotech cat n° 100-18B)
BMP2 (Human recombinant R&D system)
dispase (Invitrogen cat n° 17105041)
collagenase CLS2 (Invitrogen cat n° 17104-019)
SU5402 (calbiochem cat n° 572630)
CD15 microbeads (MACS sorter Miltenyi cat n° 130-046-601)
Anti-SSEA4 and anti-TRA 1-60 (Chemicon cat n° 90231 and 90232, respectively)
Anti-Oct-4 (Santa Cruz, cat n° sc-9081)
anti-CD15-FITC antibody from BD Bioscience (IgM clone MMA cat n° 340703)
RNA extraction kit (Mini RNA Isolation II Kit™ Zymo Research, cat n° R1033)
Real time PCR reagent: LightCycler® FastStart DNA MasterPLUS SYBR Green I (Roche cat n° 3515885)
Equipment
Low attachment dishes (NUNC™ Low Cell Binding Plates cat n° 1453)
Sterile cell culture dishes and pipettes
500 ml Filtration unit 0.2 µm Nalgene cat n° 162-0020
A real time QPCR thermocycler (Roche LightCycler 1.5)

Example 1

Culture of Primate ES Cells

Primate ES cell lines require feeder cells (Mouse Embryonic Fibroblasts (MEF) prepared from E14 mouse embryos) and FGF2 to maintain their pluripotency.

1—MEF are cultured for 3 or 4 passages and treated for 2 hours with 10 µg/ml mitomycin; cells are washed twice with PBS, trypsinised for 5 min and plated in gelatin (0.1%)-coated plates at a density of 40,000 cells/cm².

2—Primate embryonic stem cells are thawed out quickly in warm propagation medium, spun down at 800 rpm for 4 min, and resuspended to be plated on feeder cells cultured overnight with ES cell medium without FGF2. Add FGF2 to the plate.

3—Rhesus ES cells (ORMES-2 given by Dr S Mitalipov, Dr Wolf's laboratory) and Human ES cell lines HES cell lines from D Melton's laboratory [39] and I6 cell lines from the Technion Institute [40] (NIH approved) are then cultured on MEF using KO™-DMEM medium supplemented with mercaptoethanol, glutamine, non essential amino acids, 15% KOSR and 10 or 5 ng/ml FGF2 respectively (see Table 1). For Rhesus ES cells [41], 20% of F12 medium supplements the KO™-DMEM.

4—Medium is changed every day.

5—Cell colonies are dissociated into single cells or small cell clusters every 4-5 days using trypsin (HUES) or collagenase (I6, ORMES-2, 6, 9, 18), respectively (see paragraph "BOX1").

It is preferred to never let the ES cells colonies reaching confluency in the dish. Split them at about 70% confluency.

Example 2

Protocol to Direct the Fate and to Differentiate Primate ES Cells Toward a Cardiac Lineage 1—Primate ES cells are treated one or two days following the passaging for 48 H with 10 ng/ml BMP2 in the presence of 1 µM SU5402 a FGF receptor inhibitor, in KO™-SR DMEM. It is critical that the cells do not reach too much confluency at the end of the treatment.

It is preferred to resuspend BMP2 at 1 mg/ml in aqueous buffer containing at least 0.1% BSA to prevent adsorption to the vial at pH 5 or lower (due to its low solubility at neutral pH) and stored as aliquot at −20° C. Frozen stocks at 10 µg/ml can be further made in PBS. Do not freeze/thaw.

2—Embryoid bodies are generated after dispase used at 1 mg/ml for 15 min at 37° C. (HUES1, 9, 24, 26) or collagenase CLS2 (I6) dissociation of HUES cell colonies and cell aggregation in low attachment dishes in KO™-DMEM, 5% SR. $6.10^6$ to $10^7$ cells are required to fill a low attachment B6 plate to allow for formation of EBs.

It is preferred to use mechanical cell dissociation after dispase or collagenase step with a 5 ml pipette to generate small (20-50 cells) cell clusters. Spin down the cells and resuspend them in 5% SR-KO™-DMEM (Differentiation medium).

3—The functional index of cardiac differentiation in vitro is the score of beating EBs, observed after 3-4 weeks (FIG. 1). At earlier days, the kinetic of HES cell differentiation is monitored by real time PCR of cardiac transcription factors [42]. In vivo experiments (i.e., cell xenograft in immunocompromised postmyocardial infarcted rats) also serves as a functional index of cardiomyocytes derived from this protocol [42].

Generation and Selection of Cardiovascular Progenitors

1—Primate stem cells are treated for 96 hrs with 10 ng/ml BMP2 in RPMI supplemented with 2% B27, and (1 µM SU5402 (research grade) or 5 µM SU11548, SUTENT (clinical grade)).

It is preferred that the cells do not reach confluency at the end of BMP2 treatment. It is also preferred that BMP2 is added as soon as small colonies of ES cells appear.

2—Use FACS analysis using an anti-CD15-FITC antibody to visualize SSEA-1 (CD15) positive cells (FIG. 2). Cells can thus be sorted out using CD15-coated Miltenyi beads (Kit) as follows.

3—Cells are trypsinized and filtered on a 70 µm mesh nylon filter.

4—Cells are incubated for 30 min at 4° C. with gentle occasional agitation with anti-CD15 antibody-coated Miltenyi beads (100 µl/$5.10^6$ cells) in PBS supplemented with 0.5% BSA and 2 mM EDTA.

5—Cells are transferred to a L50 Miltenyi cartridge set on the magnet.

6—Cells are washed three times with 3 ml D-PBS-BSA/EDTA and allowed to be eluted from the column removed from the magnet using 3 ml of D-PBS/BSA/EDTA. The cells which go through are recycled to the cartridge on the magnet and eluted once more. This procedure is repeated three times. Counting the cells revealed 50-60% of CD15 positive cells.

7—Gene expression profile is performed by RT-real time Q-PCR (see paragraph "BOX2"). A phenotypic analysis of the CD15-positive cells revealed that they express early mesodermal (Brachyury, Tbx6) and cardiac and cardiovascular (Tbx20, Mef2c, GATA4, Isl1, Tbx18, Flk1) markers (FIGS. 3A-3D) NRx2.5 was absent in the CD15 negative while detected in the CD15 positive cell population. The CD15 positive cell population looses expression of pluripotency gene (Lefty, Nanog, Crypto). However, this cell population still over-expresses Oct-4A [43, 44].

When cultured on MEF, CD15-positive cells retained the phenotype of cardiovascular progenitors as monitored by immunstaining cardiovascular markers; when treated with VEGF (10 or 50 ng/ml) or PDGF (10 or 50 ng/ml), CD15+ become endothelial and smooth muscle cells respectively. When cultured on human cardiac fibroblasts, CD15+ cells differentiate into actinin-positive cardiomyocytes.

Example 3

Culture of Primate ES cells in a Clinical Grade Medium

Embryonic stem cells are cultured on irradiated adult human skin fibroblasts
(FSBT from Dr O. Damour, Hôpital E Herriot, Lyon) in KO™-DMEM supplemented with:
7.5% of total human freeze-thawed platelet lysate,
heparin (1000 UI/ml)
10 ng/ml FGF2 and insulin
10 passages in such a medium do not affect expression of markers of pluripotency (FIGS. 4A-4B).
FSBT are cultured in DMEM glutamine supplemented with 10% foetal calf serum (batch approved by AFSSAPS).

TABLE 1

| Propagation and differentiation medium HES cells | |
|---|---|
| KnockOut ™-DMEM | 400 ml or KO ™-DMEM 320 ml + 80 ml F12 (ORMES) |
| Glutamine 200 mM | 5 ml |
| Non essential amino acid 100 mM | 5 ml |
| MercaptoEthanol $1 \times 10^{-4}$ M | 500 µl (Use the stock $10^{-4}$ M solution for one month only) |
| Serum replacement | 15% (5% for cell differentiation) |
| Medium is filtered on 0.2 µm Nalgene Filter unit | |
| FGF2 (for ESC propagation only) | 5 or 10 ng/ml |

Human PCR Primer Sequences (See Tables 2 and 3, Example 4)

BOX 1: Cell Passaging

It is preferred that all media, enzymes, PBS should be warmed up at 37° C. Primate ES cells are very sensitive to change in temperature and should remain as long as possible at 37° C.

ORMES splitting: replace the culture medium by KO™-DMEM with 1 mg/ml collagenase (500 µl or 2.5 ml is enough for one well of a 6wells dish or for a B10 plate). Incubate the plate at 37° C. for 5 min. Add 1 or 5 ml propagation medium without FGF2 and scrape the cells with a 5 ml pipette. Transfer the cells to a 15 ml falcon tube and spin them down at 800 rpm for 4 min at RT. Aspirate the supernatant and resuspend the cells with propagation medium with FGF2. Break down the ES cells colonies by pipetting them forth and back 3 to 5 times until getting a homogenous cell suspension. Plate the cells 1/6.

I6 cell line splitting: use the same protocol as above but incubate the cells in the presence of collagenase for 45 to 60 min.

HUES cells splitting: Wash the cells once with warm PBS and add trypsin (500 µl or 2.5 ml is enough for one well of a 6 wells dish or a B10 plate). Incubate the cells under the hood for exactly 3 min. Wash out trypsin and resuspend the cells with propagation medium slightly by flushing out the feeder cell layer. Plate the cells at 1/6.

BOX 2: RT-PCR and Real Time Quantitative PCR

Total RNA is prepared after cell lysis using a kit (Zymo research). After reverse transcription using the reverse transcriptase Superscript 2 (Invitrogen) according to the manufacturer instructions, Real time PCR is carried out using a set of gene specific primers (see Tables 2 and 3). 2-6 ng cDNA is used for real time quantitative PCR, performed with a lightcycler1.5 and the SYBR Green fast start kit (Roche, Germany). The 12-µl reaction mix contained 1 µl of Master SYBR Green I mix, including Taq DNA polymerase, buffer, deoxynucleoside trisphosphate mix, SYBR Green I dye, 3 mM $MgCl_2$ and 0.5 µM of each primer. 2 µl of 10-fold diluted cDNA is added to the mixture. Data are normalised using RT-PCR of the GAPDH mRNA as an index of human cDNA content after reverse transcription. Amplification includes an initial denaturation at 95° C. for 8 min, and 45 cycles of denaturation at 95° C. for 3 s, annealing at 65° C. for 8-10 s, and extension at 72° C. for 7-10 s. The temperature transition rate is 20° C./s. Fluorescence is measured at the end of each extension step. After amplification, a melting curve is acquired by heating the product at 20° C./s to 95° C., then cooling it at 20° C./s to 70° C. The reaction was maintained at 70° C. for 20 s followed by slow heating at 0.3° C./s to 95° C. Melting curves are used to determine the specificity of PCR products, and they are further confirmed by gel electrophoresis.

Example 4

Differentiation In Vivo of Cardiac Committed Human Embryonic Stem Cells in Post-Myocardial Infarcted Rats A) Materials and Methods Real-Time Quantitative PCR by SYBR Green Detection RNA was extracted from HES cells or slices of rat myocardium using a Quiagen kit. One µg of RNA was reverse-transcribed using the Mu-MLV reverse transcriptase (Invitrogen, Cergy, France) and oligo(16)dT.

Real-time quantitative PCR was performed using a Light Cycler (Roche Diagnostic) or a Chromo4 thermal cycler (Biorad). Amplification was carried out as recommended by the manufacturers. Twelve or Twenty two µl reaction mixture contained 10 or 20 µl of Roche or Abgene SYBR Green I mix respectively (including Taq DNA polymerase, reaction buffer, deoxynucleoside trisphosphate mix, and SYBR Green I dye, 3 mM MgCl2), 0.25 µM concentration of appropriate primer and 2 µl of cDNA. The amplification programme included the initial denaturation step at 95° C. for 15 or 8 min, and 40 cycles of denaturation at 95° C. for 10 s, annealing at 65° C. for 8 s (Light cycler) or 20 s (Chromo4), and extension at 72° C. for 8 or 30 s. The temperature transition rate was 20 (Light Cycler) or 4 (Biorad)° C./s. Fluorescence was measured at the end of each extension step. After amplification, a melting curve was acquired by heating the product at 20 or 4° C./s to 95° C., cooling it at 20 or 4° C./s to 70° C., keeping it at 70° C. for 20 s, and then slowly heating it at 20 or 4° C./s to 95° C. Fluorescence was measured through the slow heating phase. Melting curves were used to determine the specificity of PCR products, which were confirmed using conventional gel electrophoresis. Data were analysed according to Pfafll et al. [16]. Primers specific for human genes are described in Tables 2 and 3.

TABLE 2

| PCR primer sequences Table 2: PCR primer sequences |||
| --- | --- | --- |
| Genes | Forward (SEQ ID NO:) | Reverse (SEQ ID NO:) |
| β-tubulin | CCGGACAGTGTGGCAACCAGATCGG (1) | TGGCCAAAAGGACCTGAGCGAACGG (2) |
| Nkx2.5 | CATTTACCCGGGAGCCTACG (3) | GCTTTCCGTCGCCGCCGTGCGCGTG (4) |
| Mef2c | AGATACCCACAACACACCACGCGCC (5) | ATCCTTCAGAGAGTCGCATGC (6) |
| SRF | CTCCGCCCCGCTCAGACCCCACCACAGA (7) | AGGTAGTTGGTGATGGGGAAGGA (8) |
| α-actin | CTATGTCGCCCTGGATTTTGAGAA (9) | TGAGGGAAGGTGGTTTGGAAGAC (10) |
| Oct-4 | ACGACCATCTGCCGCTTTGAG (11) | GCCTCTCACTCGGTTCTGAT (12) |
| Tbx6 | AGGCCCGCTACTTGTTTCTTCTGG (13) | TGGCTGCATAGTTGGGTGGCTCTC (14) |
| Isl1 | CATCGAGTGTTTCCGCTGTGTAG (15) | GTGGTCTTCTCCGGCTGCTTGTGG (16) |
| FoxH1 | GCCCCTGCCCACGCTGTCTA (17) | GGTACCTCTTCTTCCTCCTCTT (18) |
| Brachyury | CGGAACAATTCTCCAACCTATT (19) | GTACTGGCTGTCCACGATGTCT (20) |
| Mesp1 | CTCGTCTCGTCCCCAGACT (21) | AGCGTGCGCATGCGCAGTT (22) |
| Tbx20 | CTGAGCCACTGATCCCCACCAC (23) | CTCAGGATCCACCCCCGAAAAG (24) |
| Gata4 | GGTTCCCAGGCCTCTTGCAATGCGG (25) | AGTGGCATTGCTGGAGTTACCGCTG (26) |
| Pax6 | GCCAGCAACACACCTAGTCA (27) | TGTGAGGGCTGTGTCTGTTC (28) |

TABLE 2-continued

PCR primer sequences Table 2: PCR primer sequences

| Genes | Forward (SEQ ID NO:) | Reverse (SEQ ID NO:) |
|---|---|---|
| α-FP | ACTGCAATTGAGAAACCCACTGGAGATG (29) | CGATGCTGGAGTGGGCTTTTTGTGT (30) |
| Cx43 | TACCATGCGACCAGTGGTGCGC (31) | GAATTCTGGTTATCATCGGGGAA (32) |
| GAPDH | ATGGGCAAGGTGAAGGTCGGAG (33) | TCGCCCGACTTGATTTTGCAGG (34) |
| Tbx5 | TACCACCACACCCATCAAC (35) | ACACCAAGACAGGGACAGAC (36) |
| LeftyA | GGGAATTGGGATACCTGGATTC (37) | TAAATATGCACGGGCAAGGCTC (38) |
| TDGF1 | ACAGAACCTGCTGCCTGAAT (39) | ATCACAGCCGGGTAGAAATG (40) |
| Nanog | CAAAGGCAAACAACCCACTT (41) | TCTGCTGGAGGCTGAGGTAT (42) |

TABLE 3

PCR primer sequences: Melting T° (° C.) and Genbank Reference sequence

| Genes | Melting T° (° C.) | Refseq ID |
|---|---|---|
| GAPDH | 87 | AF261085; NM_002046 |
| Nkx2.5 | 88 | AB021133 |
| Mef2c | 86 | NM_002397; AL833268 |
| Oct-4A | 90 | NM_002701 |
| Tbx6 | 88 | AJ007989; NM_004608, NM_080758 |
| Brachyury | 92 | AJ001699; NM_003181 |
| Tbx20 | 88 | AJ237589; NM_020417 |
| Tbx5 | 85 | U89353; NM_080717 |
| LeftyA | 89 | U81523; NM_003240 |
| TDGF1 | 90 | M96955; NM_003212 |
| Nanog | 84 | AB093576; NM_024865 |
| Pax6 | 85 | AY707088; NM_001604 |
| α-FP | 88 | V01514 |

B) Culture and Cardiac Commitment of Human Embryonic Stem Cells

HUES-1 and I6 cell lines were cultured on Mouse Embryonic Fibroblasts (MEF) prepared from E14 mouse embryos using KO™-DMEM medium supplemented with mercaptoethanol, glutamine, non essential amino acids, 15% KO™SR and 10 or 5 ng/ml FGF2 respectively. Medium was changed every day. Cell colonies were dissociated into single cells or cell clusters every 4-5 days using trypsin (HUES-1) or collagenase (I6), respectively. A similar enzymatic digestion was used prior to cell transplantation in infarcted rats.

HES cells were treated for 48 hrs with 10 ng/ml BMP2 in the presence or absence of 1 µM SU5402, a FGF receptor inhibitor, in low KO™SR (5%) containing KO™-DMEM. Embryoid bodies were generated after trypsinisation (HUES-1) or collagenase (I6) dissociation of HES cell colonies and cell aggregation in low attachment dishes (Nunc) in DMEM, 10% foetal calf serum.

C) Myocardial Infarction Model

Myocardial infarction was induced in female Wistar (mean weight of 250 g) by ligation of the left coronary artery. Rats were operated on under general anaesthesia with isoflurane (Baxter), 3% at induction and 2% for maintenance. After tracheal intubation, mechanical ventilation (Alphalab, Minerve) was set at a rate of 70/min and with an 0.2 ml average insufflate volume. Analgesia was performed with a 10 mg/kg subcutaneous injection of ketoprofen (Merial).

The heart was exposed through a left thoracotomy and the left coronary artery was permanently snared between the pulmonary artery trunk and the left atrial appendage.

D) Rats Randomization and Myocardial Cell Injection

On the 15th day following infarction, the rats were reoperated on by median sternotomy and randomized to receive injections of BMP2-treated HUES-1 cells ($3 \times 10^6$ HUES-1 cells, n=11 rats) in suspension of single cells, BMP2-treated I6 ES cells ($3\ 10^6$ I6 cells, n=11 rats) in suspension of small cell clusters or control medium (n=9 rats). Additional animals (n=5 rats) received in-scar injections of $3\ 10^6$ HUES-1 cells that had been exposed to both BMP2 and SU5402. We selected HUES-1 cell line for the latter experimental situation since this is the one which is not already committed to the mesoderm. One rat of each group (HUES-1 cell- and I6 cell-transplanted) died within 48 hrs after cell injection.

Immunosuppressive therapy, consisting in one daily 10 mg/kg subcutaneous shot of cyclosporine A, was started on the same day and continued until sacrifice.

E) Histopathology

Myocardial sections were stained with eosin and hematoxylin using a standard protocol.

Two months after myocardial injection, rats were euthanized after general anaesthesia. Transverse-cut rat hearts were immediately fixed in OTC (Tissutec) and frozen at −180° C. nitrogen. Eight µm sections were cut on an ultramicrotome (LM 1850, Leica).

Potential tumor growth was assessed with 8 µm standardized sections stained with hematoxylin and eosin.

Immunofluorescence of myocardial cryosections were performed after paraformaldhehyde fixation and permeabilisation using Triton X-100 with an anti-human ventricular β-myosin heavy chain (MHC) (Chemicon), anti-human lamin A/C (Novacastra) anti-atrial natriuretic peptide (ANP, Abgent) and anti-Connexin 43 (Cx43) (SIGMA) antibodies. The proteins were revealed using alexa-conjugated antibodies. Sections were observed in confocal microscopy (ZEISS LSM-510 meta).

In addition, a whole-body autopsy of each transplanted rat, including brain, lungs, liver, spleen, pancreas, kidneys, periaortic lymph nodes, thymus, spine and ovaries, was systematically performed for the detection of a tumor.

F) Results

1) Phenotype of Undifferentiated I6 and HUES-1 Cell Lines

We used both HUES-1 and I6 HES cell lines to test their cardiogenic potential in vitro and in vivo. Indeed, a real-time PCR amplification of a few mesodermal and cardiac genes in both cell lines showed that the I6 cell line featured a higher basal expression of both mesodermal (Tbx6, SRF, Mesp1, brachyury) and early cardiac (Isl1, Mef2c, Tbx20) genes. GATA4 was weakly expressed in I6 but not in HUES-1 cells.

NRx2.5 was barely detected in either I6 or HUES-1 cell lines. Oct-4 level was not significantly different between both cell lines (FIG. 5).

2) Cardiac Commitment of HES Cells

Both I6 and HUES-1 Human ES cells were treated for 48 hrs with 10 ng/ml human recombinant BMP2. Gene induction was tested using real time Q-PCR. FIGS. 6A and 6B shows that both mesodermal (i.e., SRF, Tbx6, FoxH1, Isl1) and cardiac (Mef2c, NRx2.5, α-actin) genes were induced by the morphogen in HUES-1 cells. This effect was further enhanced by 3-10 folds when BMP2 was added in the presence of the FGF-R inhibitor SU5402. No significant difference was observed in the extent of the BMP2 cardiogenic response between both cell lines (FIG. 6A) although the total number of copies of each gene expressed following BMP2 induction was much higher (i.e. 10-15 fold) in I6 than in HUES-1 cell line (data not shown).

To test whether BMP2-induced HES cell commitment was translated into a process of cardiac differentiation and to envision the differentiation scenario that might take place in vivo, control or BMP2-challenged HUES-1 cells were allowed to aggregate to form embryoid bodies (EBs). Gene expression was then monitored in day 2 and day 5 EBs. BMP2 effect was observed at day 2 (i.e. two fold increase in gene expression) and became prominent at day 5 (FIG. 6B). At that stage of development, expression of both mesodermal and cardiac genes was dramatically increased by 3 to 10 folds (FIG. 6). In contrast, Oct-4 was downregulated and almost absent in EBs generated from BMP2-treated ES cells. Similar results were obtained using I6 cell line.

3) Engraftment of Cardiac Committed Cells in Post-Infarcted Rat Heart

Two months after coronary artery ligation, Human α-actin mRNAs were identified in transplanted hearts but not in those injected with the control medium (FIG. 7). In contrast, we could not detect any mRNA encoding Oct-4, Pax6 (an early ectodermal marker) or α-foeto protein, an early endodermal marker (data not shown).

Immunostaining with an anti-ANP and anti-human lamin antibodies revealed the presence of lamin-positive human ES cell derived-cardiomyocytes (FIG. 8A).

Figure 8D:
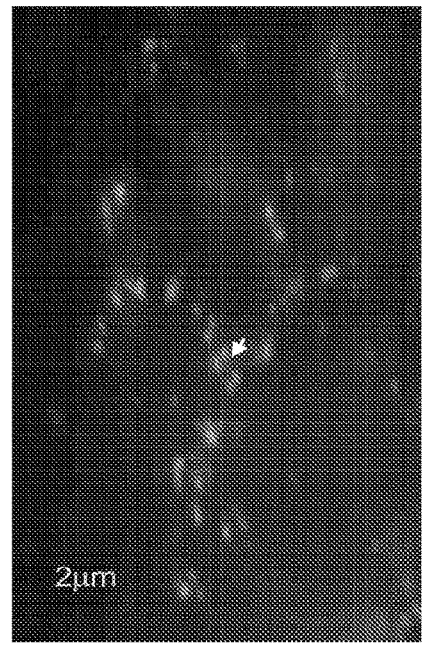

To further define the phenotype of ES cell-derived cardiomyocytes, sections were immunostained with an anti-human β-MHC antibody. These experiments revealed the presence of differentiated cardiomyocytes (FIG. 8B) in 40% and 71% of cryosections examined from HUES-1- and I6-engrafted hearts, respectively and in 85% of sections examined from rat grafted with HUES-1 cells treated with both BMP2 and SU5402. The cell engraftment was however limited. BMP2 treated HUES-1, I6 and BMP2/SU5402 HUES-1 treated ES cell-derived cardiomyocytes colonized 2.4±0.3, 3.1±0.4 and 3.6±0.3% of the scar (n=10) (FIG. 8C), respectively. Careful examination of these sections further indicated that these cardiomyocytes were still at a foetal stage demonstrated by a shorter sarcomeric length (1.6±0.1 μm) compared to 2±0.1 μm in adult rat (FIG. 8D).

Eosin-hematoxylin stained sections did not show any sign of inflammation or cell hyperproliferation two months post-transplantation (FIG. 9). Likewise, whole-body autopsies failed to disclose any tumor in peripheral organs.

Example 5

Generation of CD15+ Cardiovascular Progenitors from Human iPS Cell Line

Human iPS cell line 111, were generated using human dermal fibroblasts infected by lentivirus harbouring the cDNAs encoding Oct4, Sox2, Lin 28, Klf4 and Nanog.

Following 6 days treatment with 10 ng/ml BMP2 and 1 uM SU5402, iPS cells were trypsinised and incubated for 30 min with anti-CD15 conjugated magnetic beads (Miletenyi) and sorted out using Miltenyi columns. A fraction of BMP2-treated cells were used prior to sorting for FACS analysis using the anti-CD15 FITC and anti-cardiac markers antibodies (FIGS. 10A and 10B). 38% of cells turned out to be CD15+. This percentage was used to normalise the percentage of cells positive for the cardiac markers (numbers in green). Cells were then plated on mouse embryonic fibroblasts in KODMEM added with KOSR (invitrogen), glutamine, non essential amino acids and mercaptoethanol (HES propagation medium) and stained one week later with anti-isl1, -NRx2.5 and -Mef2c. A similar pattern of expression of cardiac proteins (i.e., NRx2.5, Mef2c, Tbx5 and Isl1) as well as endothelial marker CD31 were found in CD15+ cells derived cells as assessed by FACS analysis (FIG. 1A) and immunofluorescence (FIG. 10B).

Here the inventors also demonstrate that CD15+ cardiovascular progenitors could also be derived from iPS cells.

Discussion

This study reveals that HES cells or embryonic-like state cells (iPS cells) are capable to differentiate into cardiomyocytes without formation of teratomas after commitment toward a cardiac lineage using the cardiogenic factor BMP2. While BMP2 was shown to improve late cardiac differentiation of already differentiating cells [17], our study reports the strong instructive action of the morphogen on undifferentiated HES cells.

BMP2 is a potent mesodermal and cardiogenic instructor when used at low concentration. Its cardiogenic potential is a well conserved property throughout the evolution. Dpp, the *drosophila* homo log of BMP2, favours formation of the mesoderm including the heart [18]. Similar effects have been observed in zebrafish [19], *Xenopus* [20-21] and chicken [22]. Our data obtained in two separate cell lines uncovered that BMP2 function is conserved in human species. While I6 cells were more prone to give rise to a mesodermal lineage (FIG. 5), maximal BMP2 response was not significantly different from the one observed with HUES-1 cells although maximal extent of gene expression was higher in I6 than in HUES-1 cells. Used alone, in a defined (KOSR) medium, BMP2 effect was weak while its instructive action was dramatically enhanced by addition of the FGF receptor inhibitor, SU5402. Indeed, Human ES cells are grown on feeder cells which secrete many factors including FGF2 which is known to antagonize the BMP2 signaling pathway. SU5402 could act through at least two mechanisms to unmask the BMP2 transcriptional effect. First, FGF2 phosphorylates smad2/3, thereby preventing the BMP2 signaling co-factor from translocating into the nucleus and thus to exert its transcriptional action [23]. Second, FGF2 is also known to act as a paracrine factor on both MEF and HES cells to regulate expression of Cerberus, a nodal and BMP antagonist enriched in HES cells [24]. Finally, it might be that SU5402 blocks self-renewal of cells and favours non-specific differentiation which is further directed to the mesoderm by BMP2. By blocking all or either one of these pathways, the FGF inhibitor is required to unravel the BMP2 transcriptional response of HES cells.

In keeping with previous observations made in hearts transplanted with mouse [10, 11, 25], and human [26] ES cells, no hyperproliferation (teratoma) was observed in any of the rats injected with cardiac-committed HES cells. As intramyocardial injections in a beating heart are also known to cause leakage of a substantial proportion of cells [27], it is also noteworthy that we failed to document any extra-cardiac tumor. In fact, it was known for a long time that grafts of embryonic tissue also loose the capacity to form tumors very early after differentiation [28] when they acquire control of their proliferation by extracellular signal regulated kinases. It is thus not surprising that a similar scenario takes place after cardiac commitment of HES cells. As such, our findings are not in contradiction with the previous observation [11] that injection of HES cells into a normal immunocompetent myocardium results in teratoma formation since the latter results primarily suggest that such an environment is unlikely to provide enough cardiogenic factors required for differentiation of ES cells. Of note, the rather reassuring safety data yielded by our experiments were obtained despite the lack of pretransplantation sorting targeted at eliminating non specified cells. This suggests that the environment of the diseased myocardium (i.e., scar) enriched in growth factors is sufficient to drive primed ES cells toward a cardiac fate [25]. In a clinical perspective, however, such a selection step remains a major goal.

So far, two studies have assessed the effects of intramyocardial transplantation of HES cells. Both have entailed the use of embryoid body-derived cardiomyocytes into either normal myocardium [26] or acutely infarcted myocardium [29]. To make the protocol more clinically relevant, we selected a delayed timing of in-scar transplantation that tends to mimic the clinical scenario of heart failure and injected cardiac-specified but not yet fully differentiated monolayer-cultured cardiovascular progenitors. Altogether, the engraftment patterns seen after 2 months support the advantage of this cardiac commitment process before transplantation into the target scar where local signals are then expected to drive the fate of the graft further down the cardiomyocytic differentiation pathway.

We should however point out that the phenotype of HES cell-derived cardiomyocytes in situ was rather close to a foetal one. Indeed the cells still expressed β-MHC and ANP, two known markers of early stage of cardiac differentiation. The short length of the sarcomere is still characteristic of a foetal myocyte. Several reasons could account for this immature phenotype. HES cells may require a longer time (more than two months) to fully differentiate. Alternatively, the paracrine environment of the infarction scar may not provide the factors (some FGFs, Neuregulin, retinoic acid, BMP10, . . . ) [30] or signals taking place in embryogenesis to ensure a full differentiation process.

Another interesting observation is that I6 cells gave rise to larger engraftment areas than HUES-1 cells. Although both cell lines respond with the same efficiency to BMP2, I6 cells feature a higher basal expression of mesodermal cardiac genes (FIG. 5). This indicates that the cell line is already committed to the mesoderm, which is likely to account for the better cardiogenic potential in vivo. Of note, HUES-1 cells pretreated with BMP2 together with SU5402 also featured a better engraftment than HUES-1 challenged by BMP2 alone. This further emphasizes that the stage of specification is crucial to ensure a proper differentiation of ES cells in situ. The finding that the rates of scar repopulation by the grafted cells was overall low probably reflects a combination of initially insufficient cell dosing, extracardiac cell leakage at the time of injections and possible death of retained cells. Clearly, optimisation of the functional benefits of ES cells transplantation will require that each of these issues be thoughtfully addressed.

Finally, and in contrast to what has been reported in our previous studies using mouse ES cells [10, 31], we could not detect Cx43 mRNA or protein in HES cell-derived cardiomyocytes. HES-cell derived differentiated cardiomyocytes [13] did not either express Cx43 when transplanted in injured left ventricle while they did express it when co-cultured with neonatal rat cardiomyocytes [32]. The reason for this discrepancy with mouse ES cells or the ex-vivo situation is still unclear and might involve line-specific differences in the cardiogenic potential, a still early stage of cell development, a level of expression below the threshold of detection by immunostaining, a mistargeting of the protein or inhibitory signals coming from the fibrotic scar of infarcted rat myocardium to which HES cells might be highly sensitive. Finally, Human ESC were transplanted into rat hearts and that some of the cues required for the full differentiation of the cardiac-specified cells into Cx43-expressing cardiomyocytes may have been missing. This issue is under investigation in the laboratory.

Expression of Cx43 remains, however, critical to establish unequivocally as a true cardiac regeneration implies that the donor-derived cardiomyocytes can establish gap junction-supported electromechanical connections with those of the host. The formation of such a syncytium allowing graft-host synchronized beats which is critical for enhancement of contractility has not yet been achieved with adult cells, whether myogenic [33] or bone marrow-derived [34]. The demonstration that HES cells could fill this unmet need would likely be a major step for rationalizing their use in situations where patient outcomes are critically dependent on the replenishment of a new pool of contractile cells.

REFERENCES

[1]. Beltrami A P, Urbanek K, Kajstura J, Yan S M, Finato N, Bussani R, Nadal-Ginard B, Silvestri F, Leri A, Beltrami C A, Anversa P. Evidence that human cardiac myocytes divide after myocardial infarction. N Engl J Med. 2001, 344:1750-7.

[2]. Janssens S, Dubois C, Bogaert J, Theunissen K, Deroose C, Desmet W, Kalantzi M, Herbots L, Sinnaeve P, Dens J, Maertens J, Rademakers F, Dymarkowski S, Gheysens O, Van Cleemput J, Bormans G, Nuyts J, Belmans A, Mortelmans L, Boogaerts M, Van de Werf F. Autologous bone marrow-derived stem-cell transfer in patients with ST-segment elevation myocardial infarction: double-blind, randomised controlled trial. Lancet, 2006, 367:113-21.

[3]. Meyer G P, Wollert K C, Lotz J, Steffens J, Lippolt P, Fichtner S, Hecker H, Schaefer A, Arseniev L, Hertenstein B, Ganser A, Drexler H. Intracoronary bone marrow cell transfer after myocardial infarction: eighteen months' follow-up data from the randomized, controlled BOOST (BOne marrOw transfer to enhance ST-elevation infarct regeneration) trial. Circulation, 2006, 113:1287-94.

[4]. Lunde K, Solheim S, Aakhus S, Arnesen H, Abdelnoor M, Egeland T, Endresen K, Ilebekk A, Mangschau A, Fjeld J G, Smith H J, Taraldsrud E, Grogaard H K, Bjornerheim R, Brekke M, Muller C, Hopp E, Ragnarsson A, Brinchmann J E, Forfang K. Intracoronary injection of mononuclear bone marrow cells in acute myocardial infarction. N Engl J Med., 2006, 355:1199-209.

[5]. Schachinger V, Erbs S, Elsasser A, Haberbosch W, Hambrecht R, Holschermann H, Yu J, Corti R, Mathey D G, Hamm C W, Suselbeck T, Assmus B, Tonn T, Dimmeler S, Zeiher A M. Intracoronary bone marrow-derived progenitor cells in acute myocardial infarction. N Engl J Med. n 2006, 355:1210-21.

[6]. Balsam L B, Wagers A J, Christensen J L, Kofidis T, Weissman I L, Robbins R C. Haematopoietic stem cells adopt mature haematopoietic fates in ischaemic myocardium. Nature, 2004, 428:668-73.

[7]. Murry C E, Soonpaa M H, Reinecke H, Nakajima H, Nakajima H O, Rubart M, Pasumarthi K B, Virag J I, Bartelmez S H, Poppa V, Bradford G, Dowell J D, Williams D A, Field U. Haematopoietic stem cells do not transdifferentiate into cardiac myocytes in myocardial infarcts. Nature, 2004, 428:664-8.

[8]. Rosenzweig A. Cardiac cell therapy—mixed results from mixed cells. N Engl J Med., 2006, 355:1274-7.

[9]. Reinecke H, Poppa V, Murry C E. Skeletal muscle stem cells do not transdifferentiate into cardiomyocytes after cardiac grafting. J Mol Cell Cardiol., 2002, 34:241-9.

[10]. Behfar A, Zingman L, Hodgson D, Rauzier J, Kane G, Terzic A, Puceat M. Stem cell differentiation requires a paracrine pathway in the heart. FASEB J., 2002, 16:1558-1566.

[11]. Menard C, Hagege A, Agbulut O, Barro M, Morichetti C, Brasselet C, Bel A, Messas E, Bissery A, Bruneval P, Desnos M, Puceat M, Menasche P. Xenograft of cardiac-committed embryonic stem cells to infarcted sheep myocardium improves left ventricular function: A preclinical study. The Lancet, 2005, 17-23; 366(9490):1005-12.

[12]. Singla D K, Hacker T A, Ma L, Douglas P S, Sullivan R, Lyons G E, Kamp T J. Transplantation of embryonic stem cells into the infarcted mouse heart: formation of multiple cell types. J Mol Cell Cardiol., 2006, 40:195-200. Epub 2005 Nov. 8.

[13]. Laflamme M A, Gold J, Xu C, Hassanipour M, Rosler E, Police S, Muskheli V, Murry C E. Formation of human myocardium in the rat heart from human embryonic stem cells. Am J Pathol., 2005, 167:663-71.

[14]. Kolossov E, Bostani T, Roell W, Breitbach M, Pillekamp F, Nygren J M, Sasse P, Rubenchik O, Fries J W, Wenzel D, Geisen C, Xia Y, Lu Z, Duan Y, Kettenhofen R, Jovinge S, Bloch W, Bohlen H, Welz A, Hescheler J, Jacobsen S E, Fleischmann B K. Engraftment of engineered ES cell-derived cardiomyocytes but not BM cells restores contractile function to the infarcted myocardium. J Exp Med., 2006, 203:2315-27.

[15]. Pera M F, Trounson A O. Human embryonic stem cells: prospects for development. Development, 2004, 131:5515-25.

[16]. Pfaffl M W. A new mathematical model for relative quantification in real-time RT-PCR. Nucleic Acids Res., 2001, 29:e45.

[17]. Pal, R., and Khanna, A. (2007) Differentiation. 75, 112-122.

[18]. Frasch M. Intersecting signalling and transcriptional pathways in *Drosophila* heart specification. Semin Cell Dev Biol., 1999, 10:61-71.

[19]. Reiter J F, Verkade H, Stainier D Y. Bmp2b and Oep promote early myocardial differentiation through their regulation of gata5. Dev Biol., 2001, 234:330-8.

[20]. Breckenridge R A, Mohun T J, Amaya E. A role for BMP signalling in heart looping morphogenesis in *Xenopus*. Dev Biol., 2001, 232:191-203.

[21]. Shi Y, Katsev S, Cai C, Evans S. BMP signaling is required for heart formation in vertebrates. Dev Biol., 2000, 224:226-37.

[22]. Andree B, Duprez D, Vorbusch B, Arnold H H, Brand T. BMP-2 induces ectopic expression of cardiac lineage markers and interferes with somite formation in chicken embryos. Mech Dev., 1998, 70:119-31.

[23]. Massague J. Integration of Smad and MAPK pathways: a link and a linker revisited. Genes Dev., 2003, 17:2993-7.

[24]. Greber B, Lehrach H, Adjaye J. FGF2 Modulates TGF{beta} Signaling in MEFs and Human ES cells to Support hESC Self-renewal. Stem Cells, 2006, 12:12.

[25]. Behfar A, Perez-Terzic C, Faustino R S, Arrell D K, Hodgson D M, Yamada S, Puceat M, Niederlander N, Alekseev A E, Zingman L V, Terzic A. Cardiopoietic programming of embryonic stem cells for tumor-free heart repair. J Exp Med., 2007, 5:5.

[26]. Laflamme M A, Murry C E. Regenerating the heart. Nat Biotechnol., 2005, 23:845-56.

[27]. Teng C J, Luo J, Chiu R C, Shum-Tim D. Massive mechanical loss of microspheres with direct intramyocardial injection in the beating heart: implications for cellular cardiomyoplasty. J Thorac Cardiovasc Surg., 2006, 132: 628-32.

[28]. Damajanov I, Solter D, Skreb N. Teratocarcinogenesis as related to the age of embryos grafted under the kidney capsule. Roux arch. Dev. Biol., 1971, 173:228-234.

[29]. Kofidis T, Lebl D R, Swijnenburg R J, Greeve J M, Klima U, Robbins R C. Allopurinol/uricase and ibuprofen enhance engraftment of cardiomyocyte-enriched human embryonic stem cells and improve cardiac function following myocardial injury. Eur J Cardiothorac Surg, 2006, 29:50-5. Epub 2005 Dec. 6.

[30]. Teichmann U, Kessel M. Highly restricted BMP10 expression in the trabeculating myocardium of the chick embryo. Dev Genes Evol., 2004, 214:96-8.

[31]. Menard C, Hagege A A, Agbulut O, Barro M, Morichetti M C, Brasselet C, Bel A, Messas E, Bissery A, Bruneval P, Desnos M, Puceat M, Menasche P. Transplantation of cardiac-committed mouse embryonic stem cells to infarcted sheep myocardium: a preclinical study. Lancet, 2005, 366: 1005-12.

[32]. Kehat, I., Khimovich, L., Caspi, O., Gepstein, A., Shofti, R., Arbel, G., Huber, I., Satin, J., Itskovitz-Eldor, J., and Gepstein, L. (2004) Nat Biotechnol, 22, 1282-1289.

[33]. Leobon B, Garcin I, Menasche P, Vilquin J T, Audinat E, Charpak S. Myoblasts transplanted into rat infarcted myocardium are functionally isolated from their host. Proc Natl Acad Sci USA, 2003, 12:12.

[34]. Lagostena L, Avitabile D, De Falco E, Orlandi A, Grassi F, Iachininoto M G, Ragone G, Fucile S, Pompilio G, Eusebi F, Pesce M, Capogrossi M C. Electrophysiological properties of mouse bone marrow c-kit+ cells co-cultured onto neonatal cardiac myocytes. Cardiovasc Res., 2005, 66:482-92.

[35]. Smith, A. G. Embryo-derived stem cells: of mice and men. *Annu Rev Cell Dev Biol* 17, 435-462 (2001).

[36]. Cezar, G. G. Can human embryonic stem cells contribute to the discovery of safer and more effective drugs? *Curr Opin Chem Biol.* 11, 405-409 (2007).

[37]. Bushway, P. J. & Mercola, M. High-throughput screening for modulators of stem cell differentiation. *Methods Enzymol.* 414, 300-316 (2006).

[38]. Puceat, M. & Ballis, A. Embryonic stem cells: from bench to bedside. *Clin Pharmacol Ther.* 82, 337-339 (2007).

[39]. Cowan, C. A. et al. Derivation of embryonic stem-cell lines from human blastocysts. *N Engl J Med.* 350, 1353-1356 (2004).

[40]. Amit, M. & Itskovitz-Eldor, J. Derivation and maintenance of human embryonic stem cells. *Methods Mol Biol.* 331, 43-53 (2006).

[41]. Mitalipov, S. et al. Isolation and characterization of novel rhesus monkey embryonic stem cell lines. *Stem Cells.* 24, 2177-2186 (2006).

[42]. Tomescot, A. et al. Differentiation in vivo of cardiac committed Human embryonic stem cells in post-myocardial infarcted rats. *Stem Cells.* 25, 2200-2205 (2007).

[43]. Zeineddine, D. et al. Oct-3/4 dose dependently regulates specification of embryonic stem cells toward a cardiac lineage and early heart development. *Dev Cell.* 11, 535-546 (2006).

[44]. Stefanovic, S. & Puceat, M. Oct-3/4: not just a gatekeeper of pluripotency for embryonic stem cell, a cell fate instructor through a gene dosage effect. *Cell Cycle.* 6, 8-10 (2007).

[45]. Yao, S. et al. Long-term self-renewal and directed differentiation of human embryonic stem cells in chemically defined conditions. *Proc Natl Acad Sci USA.* 103, 6907-6912 (2006).

[46]. Takahashi K, et al., Induction of Pluripotent Stem Cells from Adult Human Fibroblasts by Defined Factors; Cell. 2007 Nov. 30; 131(5):861-72.

[47]. Nakagawa et al., Generation of induced pluripotent stem cells without Myc from mouse and human fibroblasts; Nat Biotechnol. 2008; 26(1):101-6).

[48]. Wernig et al., In vitro reprogramming of fibroblasts into a pluripotent ES-cell-like state. Nature, 2007, 448(7151): 318-24.

[49]. Maherali N et al. High-efficiency system for the generation and study of human induced pluripotent stem Cell Stem Cell 3 345-350 (2008).

The invention claimed is:

1. A method for the in vitro preparation of cardiovascular progenitor cells from mammalian pluripotent cells, wherein said method comprises:
   a) culturing mammalian pluripotent cells in a medium containing suitable agents allowing their proliferation and maintaining their pluripotency;
   b) differentiating the mammalian pluripotent cells obtained in step a) into cardiovascular progenitor cells by suspending said pluripotent cells in a medium containing BMP2 (Bone Morphogenetic Protein 2) to provide differentiated cells; and
   c) selecting and collecting the differentiated cells obtained in step b) which display the CD15 marker on their membrane surface, thereby producing cardiovascular progenitor cells from mammalian pluripotent cells.

2. The method according to claim 1, wherein said pluripotent cells are induced from adult somatic cells.

3. The method according to claim 2, wherein said pluripotent cells are induced from adult fibroblasts.

4. The method according to claim 3, wherein said pluripotent cells are induced from dermal fibroblasts infected by lentivirus harboring the cDNAs encoding Oct4, Sox2, Lin 28, Klf4, and Nanog.

5. The method according to claim 1, wherein the medium of step a) comprises a platelet lysate or a lysate of platelet-rich plasma (PRP).

6. The method according to claim 1, wherein the medium of step a) comprises a platelet lysate to wholly or partly replace the foetal animal serum usually present in the medium used for culturing primate ES cells.

7. The method according to claim 1, wherein said mammalian pluripotent cells are selected from the group consisting of primate pluripotent cells, mouse pluripotent cells, and rat pluripotent cells.

8. The method according to claim 7, wherein said primate pluripotent cells are human pluripotent cells.

9. The method according to claim 1, wherein in step b) said BMP2 is a human BMP2.

10. The method according to claim 1, wherein in step b) the medium further contains a receptor tyrosine kinase (RTK) inhibitor.

11. The method according to claim 10, wherein said RTK inhibitor is selected from the group consisting of a FGFR (fibroblast growth factor receptor) and a multitargeted tyrosine kinase receptor inhibitor, wherein said RTK inhibitor inhibits the tyrosine kinase activity of the VEGF (vascular endothelial growth factors) receptor, VEGFR-1, VEGFR-2, fetal liver tyrosine kinase receptor 3 (FLT3), KIT (stem-cell factor [SCF] receptor), PDGFRα, PDGFRβ, or a combination thereof.

12. The method according to claim 10, wherein said RTK inhibitor is selected from the group consisting of SU5402 (3-[3-(2-Carboxyethyl)-4-methylpyrrol-2-methylidenyl]-2-indolinone, SU11248 (N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide), and salts thereof.

13. The method according to claim 1, wherein in step b), the pluripotent cells are treated with 10 ng/ml BMP2 (±5 ng/ml) in the presence of 1 µM SU5402 (±0.5 µM).

14. The method according to claim 1, wherein in step b), the pluripotent cells are treated with 10 ng/ml BMP2 (±5 ng/ml) in the presence of 5 μM SU11248 (±2 μM).

15. The method according to claim 1, wherein in step b), the pluripotent cells are treated for 96 hours with 10 ng/ml BMP2 in RPMT supplemented with 2% B27 and:

1 μM research grade SU5402; or

5 μM clinical grade SU11548.

16. The method according to claim 1, wherein in step a) the medium for culturing primate pluripotent cells is a basic medium supplemented with platelet lysate obtained from primate blood.

17. The method according to claim 16, wherein said platelet lysate is added to the basic medium at a concentration of 7.5% (V/V)±2.5%.

* * * * *

SEQUENCE LISTING

```
<160> NUMBER OF SEQ ID NOS: 42

<210> SEQ ID NO 1
<211> LENGTH: 25
<212> TYPE: DNA
<213> ORGANISM: artificial sequence
<220> FEATURE:
<223> OTHER INFORMATION: PCR forward primer used for beta-tubulin marker

<400> SEQUENCE: 1
ccggacagtg tggcaaccag atcgg                                          25

<210> SEQ ID NO 2
<211> LENGTH: 25
<212> TYPE: DNA
<213> ORGANISM: artificial sequence
<220> FEATURE:
<223> OTHER INFORMATION: PCR reverse primer used for beta-tubulin marker

<400> SEQUENCE: 2
tggccaaaag gacctgagcg aacgg                                          25

<210> SEQ ID NO 3
<211> LENGTH: 20
<212> TYPE: DNA
<213> ORGANISM: artificial sequence
<220> FEATURE:
<223> OTHER INFORMATION: PCR forward primer used for Nkx2.5 marker

<400> SEQUENCE: 3
catttacccg ggagcctacg                                                20

<210> SEQ ID NO 4
<211> LENGTH: 25
<212> TYPE: DNA
<213> ORGANISM: artificial sequence
<220> FEATURE:
<223> OTHER INFORMATION: PCR reverse primer used for Nkx2.5 marker

<400> SEQUENCE: 4
gctttccgtc gccgccgtgc gcgtg                                          25

<210> SEQ ID NO 5
<211> LENGTH: 25
<212> TYPE: DNA
<213> ORGANISM: artificial sequence
<220> FEATURE:
<223> OTHER INFORMATION: PCR forward primer used for Mef2c marker

<400> SEQUENCE: 5
agatacccac aacacaccac gcgcc                                          25
```

```
<210> SEQ ID NO 6
<211> LENGTH: 21
<212> TYPE: DNA
<213> ORGANISM: artificial sequence
<220> FEATURE:
<223> OTHER INFORMATION: PCR reverse primer used for Mef2c marker

<400> SEQUENCE: 6
atccttcaga gagtcgcatg c                                           21

<210> SEQ ID NO 7
<211> LENGTH: 28
<212> TYPE: DNA
<213> ORGANISM: artificial sequence
<220> FEATURE:
<223> OTHER INFORMATION: PCR forward primer used for SRF marker

<400> SEQUENCE: 7
ctccgccccg ctcagacccc accacaga                                    28

<210> SEQ ID NO 8
<211> LENGTH: 23
<212> TYPE: DNA
<213> ORGANISM: artificial sequence
<220> FEATURE:
<223> OTHER INFORMATION: PCR reverse primer used for SRF marker

<400> SEQUENCE: 8
aggtagttgg tgatggggaa gga                                         23

<210> SEQ ID NO 9
<211> LENGTH: 24
<212> TYPE: DNA
<213> ORGANISM: artificial sequence
<220> FEATURE:
<223> OTHER INFORMATION: PCR forward primer used for a-actin marker

<400> SEQUENCE: 9
ctatgtcgcc ctggattttg agaa                                        24

<210> SEQ ID NO 10
<211> LENGTH: 23
<212> TYPE: DNA
<213> ORGANISM: artificial sequence
<220> FEATURE:
<223> OTHER INFORMATION: PCR reverse primer used for a-actin marker

<400> SEQUENCE: 10
tgagggaagg tggtttggaa gac                                         23

<210> SEQ ID NO 11
<211> LENGTH: 21
<212> TYPE: DNA
<213> ORGANISM: artificial sequence
<220> FEATURE:
<223> OTHER INFORMATION: PCR forward primer used for Oct-4 marker

<400> SEQUENCE: 11
acgaccatct gccgctttga g                                           21

<210> SEQ ID NO 12
<211> LENGTH: 20
<212> TYPE: DNA
<213> ORGANISM: artificial sequence
<220> FEATURE:
<223> OTHER INFORMATION: PCR reverse primer used for Oct-4 marker
```

```
<400> SEQUENCE: 12
gcctctcact cggttctgat                                              20

<210> SEQ ID NO 13
<211> LENGTH: 24
<212> TYPE: DNA
<213> ORGANISM: artificial sequence
<220> FEATURE:
<223> OTHER INFORMATION: PCR forward primer used for Tbx6 marker

<400> SEQUENCE: 13
aggcccgcta cttgtttctt ctgg                                         24

<210> SEQ ID NO 14
<211> LENGTH: 24
<212> TYPE: DNA
<213> ORGANISM: artificial sequence
<220> FEATURE:
<223> OTHER INFORMATION: PCR reverse primer used for Tbx6 marker

<400> SEQUENCE: 14
tggctgcata gttgggtggc tctc                                         24

<210> SEQ ID NO 15
<211> LENGTH: 23
<212> TYPE: DNA
<213> ORGANISM: artificial sequence
<220> FEATURE:
<223> OTHER INFORMATION: PCR forward primer used for Isl1 marker

<400> SEQUENCE: 15
catcgagtgt ttccgctgtg tag                                          23

<210> SEQ ID NO 16
<211> LENGTH: 24
<212> TYPE: DNA
<213> ORGANISM: artificial sequence
<220> FEATURE:
<223> OTHER INFORMATION: PCR reverse primer used for Isl1 marker

<400> SEQUENCE: 16
gtggtcttct ccggctgctt gtgg                                         24

<210> SEQ ID NO 17
<211> LENGTH: 20
<212> TYPE: DNA
<213> ORGANISM: artificial sequence
<220> FEATURE:
<223> OTHER INFORMATION: PCR forward primer used for FoxH1 marker

<400> SEQUENCE: 17
gcccctgccc acgctgtcta                                              20

<210> SEQ ID NO 18
<211> LENGTH: 22
<212> TYPE: DNA
<213> ORGANISM: artificial sequence
<220> FEATURE:
<223> OTHER INFORMATION: PCR reverse primer used for FoxH1 marker

<400> SEQUENCE: 18
ggtacctctt cttcctcctc tt                                           22

<210> SEQ ID NO 19
<211> LENGTH: 22
<212> TYPE: DNA
```

-continued

<213> ORGANISM: artificial sequence
<220> FEATURE:
<223> OTHER INFORMATION: PCR forward primer used for Brachyury marker

<400> SEQUENCE: 19
cggaacaatt ctccaaccta tt    22

<210> SEQ ID NO 20
<211> LENGTH: 22
<212> TYPE: DNA
<213> ORGANISM: artificial sequence
<220> FEATURE:
<223> OTHER INFORMATION: PCR reverse primer used for Brachyury marker

<400> SEQUENCE: 20
gtactggctg tccacgatgt ct    22

<210> SEQ ID NO 21
<211> LENGTH: 19
<212> TYPE: DNA
<213> ORGANISM: artificial sequence
<220> FEATURE:
<223> OTHER INFORMATION: PCR forward primer used for Mesp1 marker

<400> SEQUENCE: 21
ctcgtctcgt ccccagact    19

<210> SEQ ID NO 22
<211> LENGTH: 19
<212> TYPE: DNA
<213> ORGANISM: artificial sequence
<220> FEATURE:
<223> OTHER INFORMATION: PCR reverse primer used for Mesp1 marker

<400> SEQUENCE: 22
agcgtgcgca tgcgcagtt    19

<210> SEQ ID NO 23
<211> LENGTH: 22
<212> TYPE: DNA
<213> ORGANISM: artificial sequence
<220> FEATURE:
<223> OTHER INFORMATION: PCR forward primer used for Tbx20 marker

<400> SEQUENCE: 23
ctgagccact gatccccacc ac    22

<210> SEQ ID NO 24
<211> LENGTH: 22
<212> TYPE: DNA
<213> ORGANISM: artificial sequence
<220> FEATURE:
<223> OTHER INFORMATION: PCR reverse primer used for Tbx20 marker

<400> SEQUENCE: 24
ctcaggatcc accccgaaa ag    22

<210> SEQ ID NO 25
<211> LENGTH: 25
<212> TYPE: DNA
<213> ORGANISM: artificial sequence
<220> FEATURE:
<223> OTHER INFORMATION: PCR forward primer used for Gata4 marker

<400> SEQUENCE: 25
ggttcccagg cctcttgcaa tgcgg    25

```
<210> SEQ ID NO 26
<211> LENGTH: 25
<212> TYPE: DNA
<213> ORGANISM: artificial sequence
<220> FEATURE:
<223> OTHER INFORMATION: PCR reverse primer used for Gata4 marker

<400> SEQUENCE: 26
agtggcattg ctggagttac cgctg                                         25

<210> SEQ ID NO 27
<211> LENGTH: 20
<212> TYPE: DNA
<213> ORGANISM: artificial sequence
<220> FEATURE:
<223> OTHER INFORMATION: PCR forward primer used for Pax6 marker

<400> SEQUENCE: 27
gccagcaaca cacctagtca                                               20

<210> SEQ ID NO 28
<211> LENGTH: 20
<212> TYPE: DNA
<213> ORGANISM: artificial sequence
<220> FEATURE:
<223> OTHER INFORMATION: PCR reverse primer used for Pax6 marker

<400> SEQUENCE: 28
tgtgagggct gtgtctgttc                                               20

<210> SEQ ID NO 29
<211> LENGTH: 28
<212> TYPE: DNA
<213> ORGANISM: artificial sequence
<220> FEATURE:
<223> OTHER INFORMATION: PCR forward primer used for a-FP marker

<400> SEQUENCE: 29
actgcaattg agaaacccac tggagatg                                      28

<210> SEQ ID NO 30
<211> LENGTH: 25
<212> TYPE: DNA
<213> ORGANISM: artificial sequence
<220> FEATURE:
<223> OTHER INFORMATION: PCR reverse primer used for a-FP marker

<400> SEQUENCE: 30
cgatgctgga gtgggctttt tgtgt                                         25

<210> SEQ ID NO 31
<211> LENGTH: 22
<212> TYPE: DNA
<213> ORGANISM: artificial sequence
<220> FEATURE:
<223> OTHER INFORMATION: PCR forward primer used for Cx43 marker

<400> SEQUENCE: 31
taccatgcga ccagtggtgc gc                                            22

<210> SEQ ID NO 32
<211> LENGTH: 23
<212> TYPE: DNA
<213> ORGANISM: artificial sequence
<220> FEATURE:
<223> OTHER INFORMATION: PCR reverse primer used for Cx43 marker
```

-continued

```
<400> SEQUENCE: 32
gaattctggt tatcatcggg gaa                                          23

<210> SEQ ID NO 33
<211> LENGTH: 22
<212> TYPE: DNA
<213> ORGANISM: artificial sequence
<220> FEATURE:
<223> OTHER INFORMATION: PCR forward primer used for GAPDH marker

<400> SEQUENCE: 33
atgggcaagg tgaaggtcgg ag                                           22

<210> SEQ ID NO 34
<211> LENGTH: 22
<212> TYPE: DNA
<213> ORGANISM: artificial sequence
<220> FEATURE:
<223> OTHER INFORMATION: PCR reverse primer used for GAPDH marker

<400> SEQUENCE: 34
tcgcccgact tgattttgca gg                                           22

<210> SEQ ID NO 35
<211> LENGTH: 19
<212> TYPE: DNA
<213> ORGANISM: artificial sequence
<220> FEATURE:
<223> OTHER INFORMATION: PCR forward primer used for Tbx5 marker

<400> SEQUENCE: 35
taccaccaca cccatcaac                                               19

<210> SEQ ID NO 36
<211> LENGTH: 20
<212> TYPE: DNA
<213> ORGANISM: artificial sequence
<220> FEATURE:
<223> OTHER INFORMATION: PCR reverse primer used for Tbx5 marker

<400> SEQUENCE: 36
acaccaagac agggacagac                                              20

<210> SEQ ID NO 37
<211> LENGTH: 22
<212> TYPE: DNA
<213> ORGANISM: artificial sequence
<220> FEATURE:
<223> OTHER INFORMATION: PCR forward primer used for LeftyA marker

<400> SEQUENCE: 37
gggaattggg atacctggat tc                                           22

<210> SEQ ID NO 38
<211> LENGTH: 22
<212> TYPE: DNA
<213> ORGANISM: artificial sequence
<220> FEATURE:
<223> OTHER INFORMATION: PCR reverse primer used for LeftyA marker

<400> SEQUENCE: 38
taaatatgca cgggcaaggc tc                                           22

<210> SEQ ID NO 39
<211> LENGTH: 20
<212> TYPE: DNA
```

```
<213> ORGANISM: artificial sequence
<220> FEATURE:
<223> OTHER INFORMATION: PCR forward primer used for TDGF1 marker

<400> SEQUENCE: 39
acagaacctg ctgcctgaat                                              20

<210> SEQ ID NO 40
<211> LENGTH: 20
<212> TYPE: DNA
<213> ORGANISM: artificial sequence
<220> FEATURE:
<223> OTHER INFORMATION: PCR reverse primer used for TDGF1 marker

<400> SEQUENCE: 40
atcacagccg ggtagaaatg                                              20

<210> SEQ ID NO 41
<211> LENGTH: 20
<212> TYPE: DNA
<213> ORGANISM: artificial sequence
<220> FEATURE:
<223> OTHER INFORMATION: PCR forward primer used for Nanog marker

<400> SEQUENCE: 41
caaaggcaaa caacccactt                                              20

<210> SEQ ID NO 42
<211> LENGTH: 20
<212> TYPE: DNA
<213> ORGANISM: artificial sequence
<220> FEATURE:
<223> OTHER INFORMATION: PCR reverse primer used for Nanog marker

<400> SEQUENCE: 42
tctgctggag gctgaggtat                                              20
```